(12) United States Patent
Fuller

(10) Patent No.: US 9,980,887 B2
(45) Date of Patent: *May 29, 2018

(54) COMPOSITIONS FOR USE IN TREATMENT OF HYPERPIGMENTATION AND METHODS OF USE THEREOF

(71) Applicant: DermaMedics, LLC, Oklahoma City, OK (US)

(72) Inventor: Bryan B. Fuller, Edmond, OK (US)

(73) Assignee: DermaMedics, LLC, Oklahoma City, OK (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/236,967

(22) Filed: Aug. 15, 2016

(65) Prior Publication Data

US 2016/0346180 A1 Dec. 1, 2016

Related U.S. Application Data

(60) Continuation of application No. 13/919,644, filed on Jun. 17, 2013, now Pat. No. 9,622,950, which is a division of application No. 12/751,728, filed on Mar. 31, 2010, now Pat. No. 9,616,006, which is a continuation of application No. PCT/US2008/079534, filed on Oct. 10, 2008.

(60) Provisional application No. 60/998,345, filed on Oct. 10, 2007, provisional application No. 61/126,478, filed on May 5, 2008.

(51) Int. Cl.
| | |
|---|---|
| A61K 31/11 | (2006.01) |
| A61K 31/222 | (2006.01) |
| A61K 31/60 | (2006.01) |
| A61K 31/05 | (2006.01) |
| A61K 8/37 | (2006.01) |
| A61K 9/06 | (2006.01) |
| A61K 31/19 | (2006.01) |
| A61K 9/00 | (2006.01) |
| A61K 9/08 | (2006.01) |
| A61K 9/20 | (2006.01) |
| A61K 31/085 | (2006.01) |
| A61K 47/24 | (2006.01) |
| A61K 8/33 | (2006.01) |
| A61K 8/34 | (2006.01) |
| A61K 8/368 | (2006.01) |
| A61Q 19/02 | (2006.01) |
| A61Q 19/08 | (2006.01) |
| A61K 8/25 | (2006.01) |
| A61K 8/35 | (2006.01) |

(52) U.S. Cl.
CPC ............ *A61K 8/37* (2013.01); *A61K 8/25* (2013.01); *A61K 8/33* (2013.01); *A61K 8/34* (2013.01); *A61K 8/347* (2013.01); *A61K 8/35* (2013.01); *A61K 8/368* (2013.01); *A61K 9/0014* (2013.01); *A61K 9/0019* (2013.01); *A61K 9/06* (2013.01); *A61K 9/08* (2013.01); *A61K 9/2059* (2013.01); *A61K 9/2063* (2013.01); *A61K 31/085* (2013.01); *A61K 31/11* (2013.01); *A61K 31/19* (2013.01); *A61K 31/222* (2013.01); *A61K 31/60* (2013.01); *A61K 47/24* (2013.01); *A61Q 19/02* (2013.01); *A61Q 19/08* (2013.01)

(58) Field of Classification Search
CPC ...... A61K 31/11; A61K 31/19; A61K 31/222; A61K 31/60; A61K 47/24; A61K 8/347; A61K 8/368; A61K 8/37; A61K 9/0014
See application file for complete search history.

(56) References Cited

U.S. PATENT DOCUMENTS

| | | | |
|---|---|---|---|
| 5,505,949 A | | 4/1996 | Benitez |
| 5,599,342 A | * | 2/1997 | Hsia ................ A61B 18/203 606/9 |
| 6,869,611 B1 | | 3/2005 | Kligman et al. |
| 6,893,647 B1 | | 5/2005 | Malton et al. |
| 2003/0124157 A1 | | 7/2003 | Engles et al. |
| 2006/0216251 A1 | | 9/2006 | Morariu |
| 2006/0222671 A1 | | 10/2006 | Weidner |
| 2007/0053849 A1 | | 3/2007 | Doyle |
| 2007/0207220 A1 | | 9/2007 | Luedtke et al. |

FOREIGN PATENT DOCUMENTS

| | | |
|---|---|---|
| DE | 20221578 U1 | 6/2006 |
| EP | 08837020.0 | 2/2011 |
| JP | 2003113071 | 4/2003 |
| JP | 2003043621 | 5/2003 |
| JP | 2004000305 | 12/2003 |
| WO | 2003043621 A1 | 5/2003 |
| WO | 2004000305 A1 | 12/2003 |
| WO | 200879534 | 12/2008 |

OTHER PUBLICATIONS

U.S. Appl. No. 13/919,644, Bryan B. Fuller, filed Jun. 17, 2013; Office Action dated Jan. 18, 2017.
Communication Pursuant to Article 94(3) EPC dated Sep. 20, 2016, in EP Application No. 08837020.0, 4 pages.
Communication Pursuant to Rule 114(2) EPC (Third Party Observations) dated Aug. 23, 2016 in EP Application No. 08837020.0, 26 pages.
Angerer, et al., SCCS Committees, Directorate-General for Health & Consumers, Scientific Committee on Consumer Safety, SCCS, "Opinion on Fragrance allergens in cosmetic products" The SCCS adopted this pre-consultation opinion at its 13th plenay meeting of Dec. 13-14, 2011, 136 pgs.

(Continued)

*Primary Examiner* — Sahar Javanmard
(74) *Attorney, Agent, or Firm* — Dunlap Codding, P.C.

(57) ABSTRACT

Compositions containing an effective dermatological disease-treating or dermatological condition-treating active agent and a pharmaceutically-acceptable carrier or vehicle are disclosed. Methods of using the compositions are also disclosed.

12 Claims, 13 Drawing Sheets
(7 of 13 Drawing Sheet(s) Filed in Color)

(56) References Cited

OTHER PUBLICATIONS

Chainey et al.; "Anethole blocks both early and late cellular responses transduced by tumor necrosis factor: effect on NF-KB, AP-I, JNK, MAPKK and apoptosis"; Oncogene 19:2911-2920 (2000).

Fujisawa et al.; "Predicting the Biological Activities of 2-Methoxyphenol Antioxidants: Effects of Dimers"; In Vivo 21:181-188 A(2007).

Little, Arthur D., Inc., "National Toxicology Program, Executive Summary of Safety and Toxicity Information, Isoeugenol" CAS No. 97-54-1 Apr. 10, 1991, 3 pgs.

Murakami, et al., "Dhydrodiisoeugenol, an isoeugenol dimer, inhibits lipopolysaccharide-stimulated nuclear factor kappa B activation and cyclooxygenase-2 expression in macrophages" Archives of Biochemistry and Biophysics, vol. 434 (2005) pp. 326-332.

Ogata et al.; "Antioxidant Activity of Eugenol and Related Monomeric and Dimeric Compounds"; Chem Pharm Bull. 48(10):1467-1469 (2000).

Park et al.; "Suppression of interleukin-2 gene expression by isoeugenol is mediated through down-regulation of NF-AT and NF-KB"; Int. Immuno. 7:1251-1254 (2007).

Tsubouch, et al.; "Inhibitory action of eugenol compounds on the production of nitric oxide in RAW264.7 macrophages"; Biomed Res. 27(2):69-74 (2006).

Zaw et al.; "Catalase restores the altered mRNA expression of collagen and matrix metalloproteinases by dermal fibroblasts exposed to reactive oxygen species"; Eur J Dermatol. 16(4):375-379 (2006).

Canadian Serial No. 2,866,527; Bryan B. Fuller, filed Oct. 7, 2014, Office Action dated Mar. 9, 2017.

Murakami, et al.; "DehydrodiIsoeugenol, an Isoeugenol Dimer, Inhibits Lipopolysaccharide-stimulated Nuclear Factor Kappa B Activation and Cyclooxygenase-2 Expression in Macrophages," Archives of Biochemistry and Biophysics, (2005), vol. 434, No. 2, pp. 326-332.

Tanaka, et al.; "Contact Allergy to Isoeugenol and its Derivatives: Problems with Allergen Substitution," Environmental and Occupational Dermatitis, (2004), vol. 51, No. 5-6, pp. 288-291.

European Application No. 17174953.4, filed Jun. 8, 2017, European Search Report and Written Opinion dated Oct. 2, 2017.

* cited by examiner

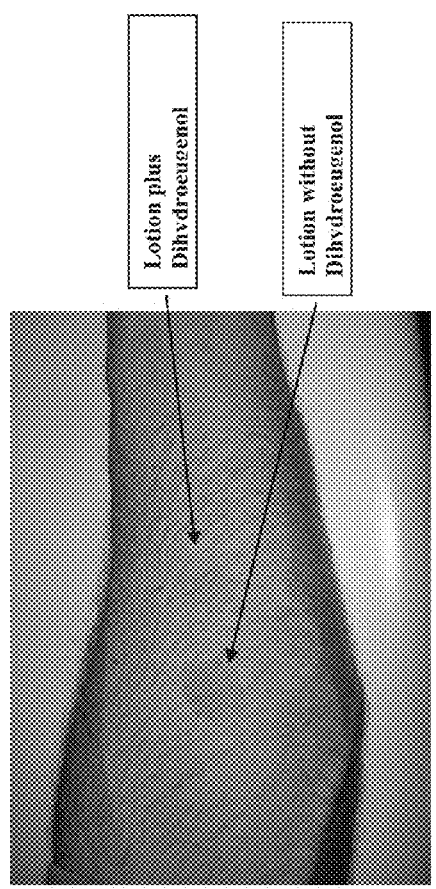
Figure 5
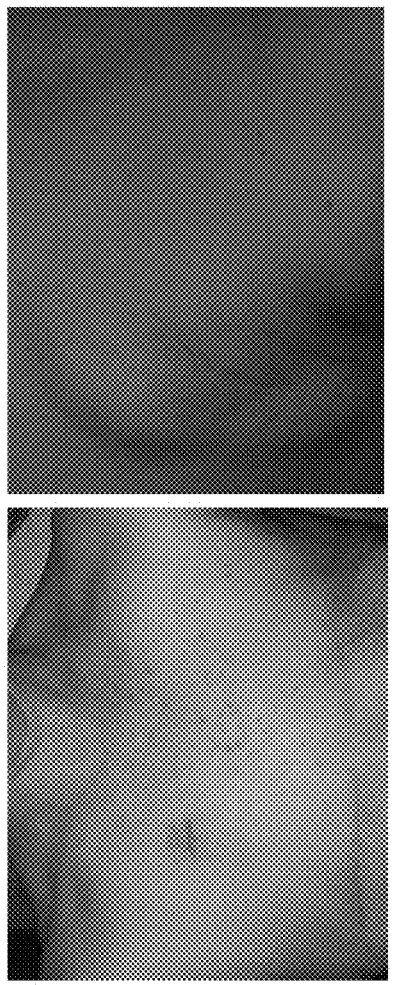
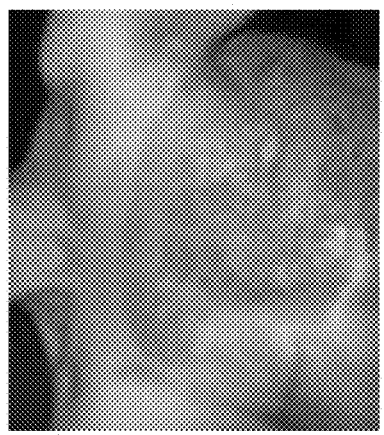
Figure 7

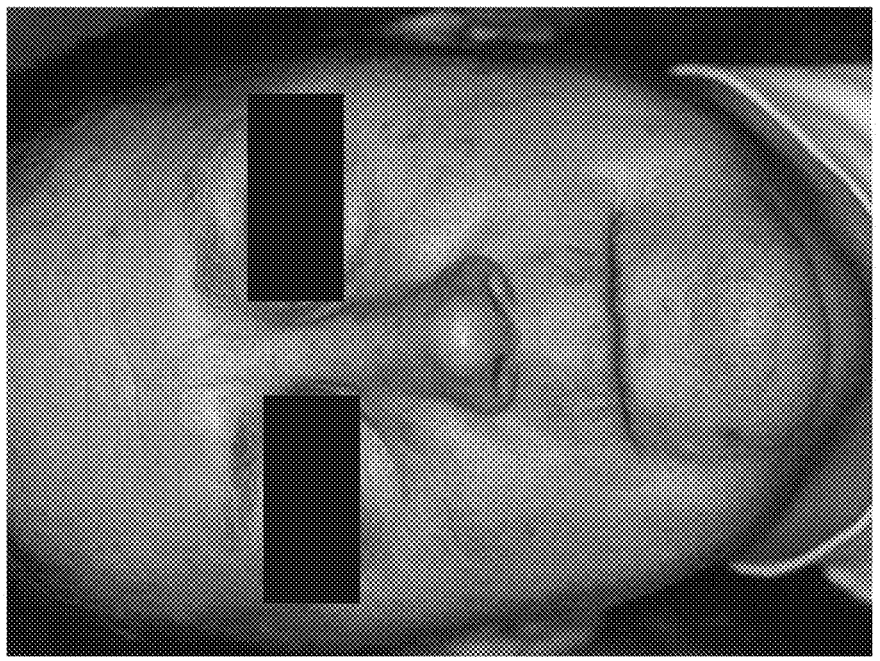
Figure 6

Depigmentation of Human Melanocytes Treated with TH-212 and TH-213

CONTROL   TH-212   TH-213

Note the pronounced loss of melanin in cells treated with either TH-212 or TH-213 for only 9 days

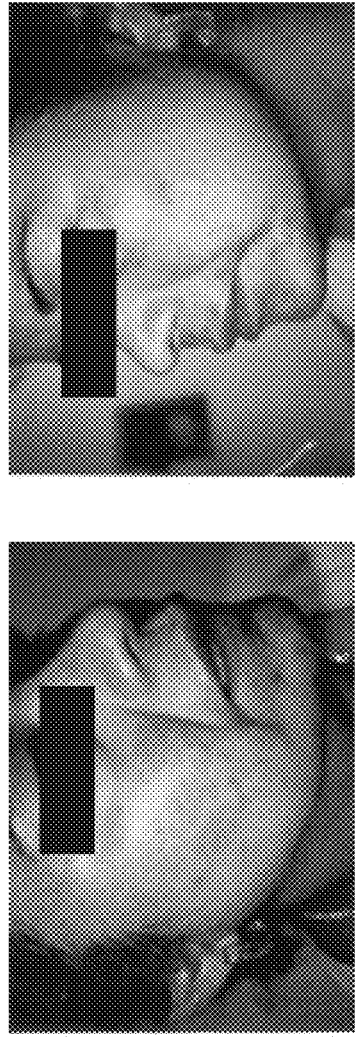
Figure 15

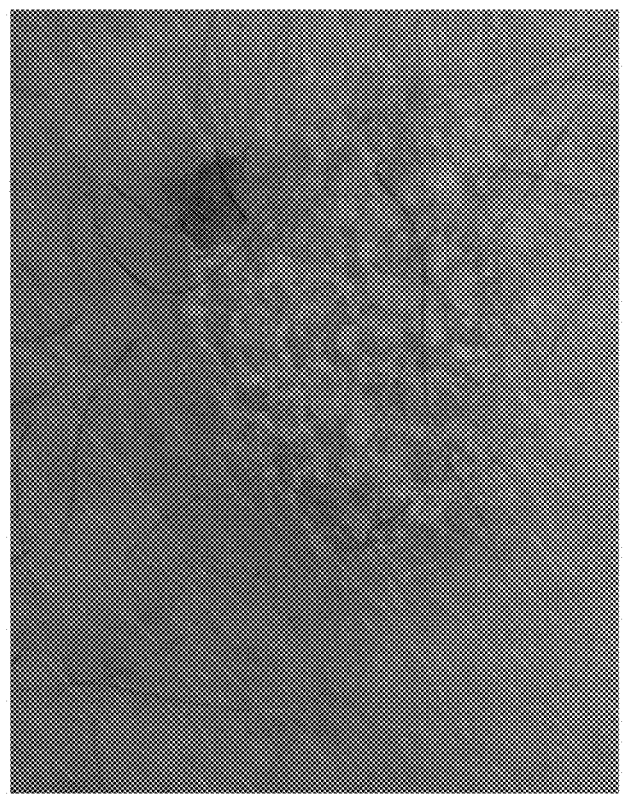
Figure 19

COMPOSITIONS FOR USE IN TREATMENT OF HYPERPIGMENTATION AND METHODS OF USE THEREOF

CROSS-REFERENCE TO RELATED APPLICATIONS/INCORPORATION BY REFERENCE STATEMENT

The present application is a continuation of U.S. Ser. No. 13/919,644, filed Jun. 17, 2013; which is a division of U.S. Ser. No. 12/751,728, filed Mar. 31, 2010; which is a continuation of International Patent Application PCT/US2008/079534, filed Oct. 10, 2008; which claims benefit under 35 U.S.C. 119(e) of U.S. Provisional Application Ser. No. 60/998,345, filed Oct. 10, 2007, and U.S. Provisional Application Ser. No. 61/126,478, filed May 5, 2008. The entirety of each of these applications is hereby expressly incorporated herein by reference.

BACKGROUND

Human skin comprises an epidermis layer, which is predominantly composed of keratinocytes and a small number of melanocytes and Langerhans cells (antigen presenting cells), and a dermis layer, which is primarily composed of fibroblasts. The majority of skin disorders involve inflammation triggered by some insult to the skin. Keratinocytes respond quickly to environmental stimuli (e.g., UV radiation (UVR), allergens, irritants or physical damage) by producing a variety of inflammatory mediators, including cytokines (e.g., IL-1, TNF-alpha, and IL-6) and chemokines (e.g., IL-8). One of the most active inflammatory mediators is PGE-2 (Prostaglandin E2) and, of course, many topical dermatology drugs have been designed to lower levels of PGE-2. The fibroblasts in the dermis also produce PGE-2 along with a variety of chemokines, cytokines and matrix destroying enzymes such as collagenase (MMP-1).

The identification of compounds that can suppress the production of inflammatory mediators in the skin would allow effective topical products to be developed to treat a variety of inflammatory skin diseases or disorders including eczema, radiation dermatitis, atopic dermatitis, actinic keratosis, seborrheic dermatitis, other dermatic diseases and acne. Compositions able to treat other dermatological conditions such as aging effects and hyperpigmentation would also be desirable.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 5 is a photograph of an arm of a human subject which was exposed to erythema-inducing UVB radiation and treated with a lotion of the presently disclosed and/or claimed inventive concept(s).

FIG. 6 shows photographs of a human subject's face which has symptoms of rosacea. Facial areas of rosacea are shown in (A) while these areas, 12 weeks after initiation of treatment with DHE, IE, and cinnamaldehyde, are shown in (B).

FIG. 7 shows the effects of topical DHE application on patients undergoing radiation treatment. (A) Radiation dermatitis in a typical radiation patient untreated for radiation dermatitis. (B) A patient was treated with a topical 2% DHE lotion daily during 35 radiation treatments. The photograph was taken after the $35^{th}$ treatment and the skin shows no evidence of radiation dermatitis. (C) A close-up photograph of the patient of (B), one month after the end of radiation treatments. There is no evidence of radiation damage to the skin.

FIG. 15 shows photographs which demonstrate how a topically-applied formulation of isoeugenol acetate (referred to in the figure as TH-212 ester) plus salicylic acid causes a clearing of acne and hyperpigmentation after a 4 week treatment.

FIG. 19 shows photographs which demonstrate psoriatic skin before (A) and after (B) treatment with a formulation comprising DHE and IE.

DETAILED DESCRIPTION

Figure 1:
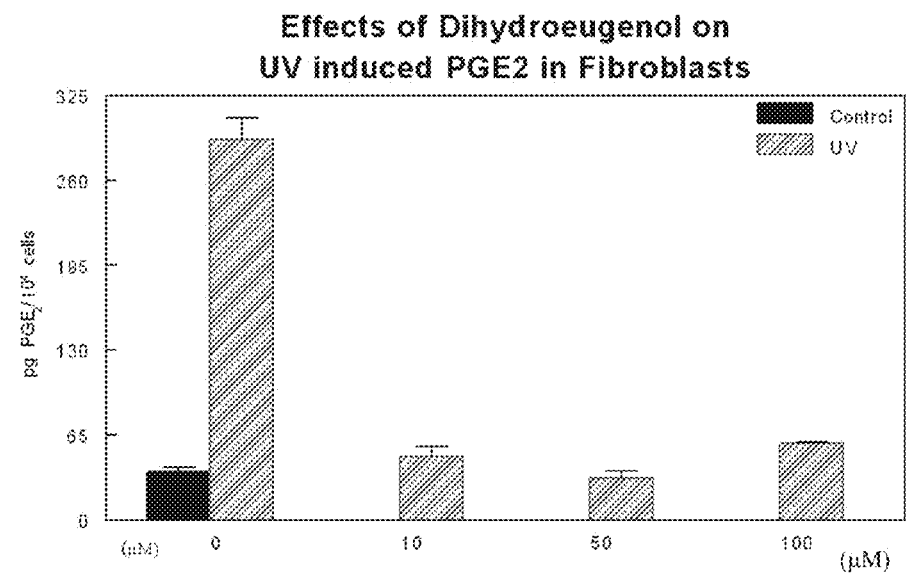
FIG. 1 is a graph showing the effects of dihydroeugenol (DHE) on UV-induced PGE-2 in fibroblasts.

The description herein of several embodiments describes non-limiting examples that further illustrate the presently disclosed and/or claimed inventive concept(s).

In the following detailed description, numerous specific details are set forth in order to provide a more thorough understanding of the disclosure. However, it will be apparent to a person having ordinary skill in the art that the presently disclosed and/or claimed inventive concept(s) may be practiced without these specific details. In other instances, features which are well known to persons of ordinary skill in the art have not been described in detail to avoid complication unnecessarily the description.

Therefore, unless defined otherwise, all technical and scientific terms used herein have the same meanings as commonly understood by one skilled in the art to which the presently disclosed and/or claimed inventive concept(s) pertains. For example, the term "plurality" refers to "two or more." The singular forms "a," "an," and "the" include plural referents unless the context clearly indicates otherwise. The term "about", where used herein when referring to a measurable value such as an amount, a temporal duration, and the like, is meant to encompass variations of ±20% or ±10%, more particularly ±5%, even more particularly ±1%, and still more particularly ±0.1% from the specified value, as such variations are appropriate to perform the disclosed methods.

Turning now to the presently disclosed and/or claimed inventive concept(s), compositions are contemplated herein that comprise compounds, in particular dihydroeugenol (DHE) and/or isoeugenol (IE) and/or ethyl vanillin (EV) or salts, esters, ethers, or derivatives thereof; also contemplated herein are methods for topically or systemically delivering them for treatment against inflammation-related and other dermatological conditions such as described herein. These DHE and/or IE and/or EV or salts, esters, ethers or derivatives thereof also are delivered to a measurable extent transepidermally and/or transdermally. In one of its method aspects, this presently disclosed and/or claimed inventive concept(s) is directed to a method for treating a patient with a dermatological disease or condition by topically administering to said patient a pharmaceutical or cosmetic composition comprising a pharmaceutically or cosmetically acceptable topical carrier and an effective dermatological disease, disorder or condition-treating amount of a formulation of DHE and/or IE and/or EV, or salts, esters, ethers, or derivatives thereof. In particular, the presently disclosed and/or claimed inventive concept(s) is directed to a method of using a composition comprising one or more of DHE and/or IE and/or EV or salts, esters, ethers, or derivatives for treating dermatologic diseases, disorders or conditions, aging effects related to decreasing production of collagen, elastin, or hyaluronic acid, or to hyperpigmentation. The formulations may further contain cinnamaldehyde.

The presently disclosed and/or claimed inventive concept(s) is directed to methods and compositions for treating a variety of skin disorders, diseases, and conditions including for example, rosacea, radiation dermatitis, erythemas (sunburns), psoriasis, atopic dermatitis, allergic and irritant contact dermatitis, actinic keratitis, acne, scarring, hyperpigmentation, and seborrheic dermatitis or eczema, or other eczemas, and alopecia areata, wherein the compounds act, for example, on skin keratinocytes and fibroblasts and on immune cells such as monocytes and on melanocytes. The presently disclosed and/or claimed inventive concept(s) further comprises methods and compositions for mitigating the effects of aging, e.g., by enhancing production of collagen, elastin and hyaluronic acid synthases in skin fibroblast cells.

Inflammatory skin diseases are the most common problem in dermatology. They come in many forms, from occasional rashes accompanied by itching and redness to chronic conditions such as dermatitis (eczema), rosacea, seborrheic dermatitis, and psoriasis. However, they are all linked by one common factor, inflammation. It has been found that the inflammatory markers (cytokines) produced by skin and immune cells that are required for the development of an inflammatory response, such as atopic dermatitis and radiation dermatitis. The presently disclosed and/or claimed inventive concept(s) comprises agents that suppress the production of a variety of inflammatory responses in cultured skin cells (keratinocytes and fibroblasts), and immune cells (monocytes and T-lymphocytes) and in intact living skin. As a result of blocking these inflammatory processes in the skin, the present compounds are able to effectively reduce or eliminate a variety of inflammatory symptoms that occur with common skin problems.

Rosacea is a vascular, inflammatory skin disorder that affects approximately 5% of the population and is characterized by frequent periods of facial redness or flushing caused by over-active capillaries. Over time, this chronic state of skin inflammation gives rise to a variety of rosacea symptoms. Rosacea is sometimes characterized mistakenly as adult-acne because patients present with a reddened face and acne-like symptoms. However, individuals affected with this skin disease also may have persistent redness with accompanying pain and itching in areas such as the forehead, chin, nose, ears, chest and back. As the disease progresses, small blood vessels and tiny pimples (called papules or pustules) begin to appear on and around the reddened area. In severe cases rosacea can affect the eyes (ocular rosacea) and cause disfigurement of the nose (rhynophyma). In addition to the physical symptoms associated with rosacea, patients also suffer significant psychological and social problems if left untreated.

Regarding skin aging, research shows that there are, in fact, two distinct types of skin aging. Aging caused by inherited genes is called intrinsic (internal) aging. The other type of aging is known as extrinsic (external) aging and is caused by environmental factors, such as exposure to the sun's rays. Intrinsic aging, also known as the natural aging process, is a continuous process that normally begins in our mid-20s. Within the skin the dermis of normal (wrinkle-free) skin is composed of abundant amounts of type I collagen and type VII collagen, as well as elastin, which provides tissue strength, resiliency and recoil. However, as the dermal fibroblasts which produce collagen and elastin begin to age, they produce decreasing amounts of these proteins. Further, aging fibroblasts produce increased amounts of enzymes called matrix metalloproteinases (MMP's), which degrade collagen and elastin. This results in a drastic loss of collagen and elastin over time and results in skin laxity and fragility, visible in the form of fine lines and wrinkles. The signs of intrinsic aging are: fine wrinkles, thin and transparent skin, loss of underlying fat, leading to hollowed cheeks and eye sockets as well as noticeable loss of firmness on the hands and neck, dry skin that may itch, graying hair that eventually turns white, and hair loss. Genes control how quickly the normal aging process unfolds. Some persons notice their first gray hairs in their 20s; others do not see graying until their 40s.

A number of extrinsic aging factors often act together with the normal aging process to prematurely age our skin. Most premature aging is caused by sun exposure. Other external factors that prematurely age our skin are repetitive facial expressions, gravity and smoking. Without protection from the sun's rays, just a few minutes of exposure each day over the years can cause noticeable changes to the skin. Freckles, age spots, spider veins on the face, rough and leathery skin, fine wrinkles that disappear when stretched, loose skin, a blotchy complexion and skin cancer can all be traced to sun exposure. "Photoaging" is the term dermatologists use to describe this type of aging caused by exposure to the sun's rays. The amount of photoaging that develops depends on: (1) a person's skin color and (2) his or her history of long-term or intense sun exposure. Persons with fair skin who have a history of sun exposure develop more signs of photoaging than those with dark skin. In the darkest skin, the signs of photoaging are usually limited to fine wrinkles and a mottled complexion.

Photoaging occurs over a period of years. With repeated exposure to the sun, the skin loses the ability to repair itself, and the damage accumulates. Scientific studies have shown that repeated ultraviolet (UV) exposure impairs the synthesis of new collagen and increases the expression of MMP enzymes, which break down collagen. The sun also causes excessive elastin production but the elastin made is abnormal and aggregates into clumps, leading to a condition referred to by dermatologists as elastosis. Due to the loss of collagen and the production of abnormal elastin, sun-weakened skin ceases to spring back compared to skin protected from UV rays. Skin also becomes loose, wrinkled, and leathery much earlier with unprotected exposure to sunlight.

While there is nothing currently available to stop the aging process, it is possible to slow the rate at which the skin ages. As described above, both intrinsic and photoaging are due to the breakdown and loss of collagen and elastin in the skin. The present compositions contain ingredients that have been scientifically proven herein to increase the production of collagen and elastin, as well as reduce the expression of MMP enzymes. These two effects slow the aging process and can even aid in rebuilding the dermal matrix, which reduces the appearance of new and existing wrinkles and fine lines.

Another skin condition, acne, is the most common skin disorder seen by doctors and affects almost everyone at some time. Teenagers are affected most often. Acne can cause a great deal of embarrassment and anxiety and can even cause people to become depressed which can lead to withdrawing from friends, and performing poorly at school or work. The exact cause of acne is unknown, but the following factors are considered important. (1) Acne is the visible end result of hormonal, bacterial and inflammatory disturbances that take place at the level of the oil pore (pilosebaceous follicle). (2) As the process advances, greater amounts of oil may be produced within the sebaceous glands, though the change in composition and quality of the oil may be more important than the quantity, the scale produced on the inside walls of the hair follicle becomes stickier and it builds up and blocks the pore which shows up as whiteheads and blackheads (comedones). (3) The acne bacteria (*Propionobacterium acnes*) grow and multiply in the retained oil. The sebum acts as a nutrition source for the bacterial, which in turn release chemicals within the pore. These alert and attract white cells from the blood leading to inflammation. (4) As these inflamed hair follicles (pores) and glands enlarge, the surrounding skin also becomes inflamed and may lead to even larger lumps and cysts (also called nodules). (5) Inflammation may damage the cells that make collagen. Less collagen production causes thinning of the skin, which is seen as depressed scars. Occasionally, collagen production will increase, which then causes the scars to become thickened. The present formulations may also be used to heal scars from acne and stretch marks by improving their structure and coloration.

Another skin disorder, psoriasis, is a chronic (long-lasting) skin disease characterized by scaling and inflammation. Scaling occurs when cells in the outer layer of skin reproduce faster than normal and pile up on the skin's surface. Psoriasis affects 2 to 2.6 percent of the United States population, or almost 5.8 to 7 million people. It occurs in all age groups and about equally in men and women. People with psoriasis may suffer discomfort, restricted motion of joints, and emotional distress. When psoriasis develops, patches of skin thicken, redden, and become covered with silvery scales. These patches are sometimes referred to as plaques. They may itch or burn. The skin at joints may crack. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis. This condition is called psoriatic arthritis.

Research indicates that psoriasis may be a disorder of the immune system. The immune system includes a type of white blood cell, called a T cell, that normally helps protect the body against infection and disease. In psoriasis, the immune system produces too many T cells, in the skin. These T cells trigger the inflammation and excessive skin cell reproduction seen in people with psoriasis. This leads to inflammation and flaking of skin. The presently disclosed and/or claimed inventive concept(s) inhibits the production of the same inflammatory mediators that other psoriasis therapies target, but since it is in topical form, it does not require frequent injections nor does it lower body's overall immune function.

Eczema is a general term for many types of skin inflammation (dermatitis). Atopic dermatitis is the most common of the many types of eczema. Several other forms have very similar symptoms. The diverse types of eczema are listed and briefly described below.

(1) Atopic dermatitis is a chronic skin disease characterized by itchy, inflamed skin. The word "dermatitis" means inflammation of the skin. "Atopic" refers to diseases that are hereditary, tend to run in families, and often occur together. These diseases include asthma, hay fever, and atopic dermatitis. In atopic dermatitis, the skin becomes extremely itchy and inflamed, causing redness, swelling, cracking, weeping, crusting, and scaling. Atopic dermatitis most often affects infants and young children, but it can continue into adulthood or first show up later in life. In most cases, there are periods of time when the disease is worse, called exacerbations or flares, which are followed by periods when the skin improves or clears up entirely, called remissions. Many children with atopic dermatitis enter into a permanent remission of the disease when they get older, although their skin often remains dry and easily irritated. Environmental factors can activate symptoms of atopic dermatitis at any time in the lives of individuals who have inherited the atopic disease trait. The cause of atopic dermatitis is unknown, but the disease seems to result from a combination of genetic and environmental factors. Evidence suggests that the disease is associated with other so-called atopic disorders such as hay fever and asthma, which many people with atopic dermatitis also have. In addition, many children who outgrow the symptoms of atopic dermatitis go on to develop hay fever or asthma. Although one disorder does not cause another, they may be related, thereby giving researchers clues to understanding atopic dermatitis. Atopic dermatitis is very common and affects males and females equally and accounts for 10 to 20% of all referrals to dermatologists. Atopic dermatitis occurs most often in infants and children and its onset decreases substantially with age. Scientists estimate that 65 percent of patients develop symptoms in the first year of life, and 90 percent develop symptoms before the age of 5. Onset after age 30 is less common and often occurs after exposure of the skin to harsh conditions. People who live in urban areas and in climates with low humidity seem to be at an increased risk for developing atopic dermatitis. About 10% of all infants and young children experience symptoms of the disease. Roughly 60 percent of these infants continue to have one or more symptoms of atopic dermatitis even after they reach adulthood. This means that more than 15 million people in the United States have symptoms of the disease.

(2) Contact eczema is a localized reaction that includes redness, itching, and burning where the skin has come into contact with an allergen (an allergy-causing substance) or with an irritant such as an acid, a detergent (soap, bodywash), or other chemical.

(3) Allergic contact eczema is a red, itchy, weepy reaction where the skin has come into contact with a substance that the immune system recognizes as foreign, such as poison ivy or certain preservatives in creams and lotions.

(4) Seborrheic eczema is a form of skin inflammation of unknown cause but which is associated with a certain type of yeast that lives on the skin. Seborrheic eczema presents as yellowish, oily, scaly patches of skin on the scalp, face, and occasionally other parts of the body (called cradle cap in infants).

(5) Nummular eczema is coin-shaped patches of irritated skin—most commonly on the arms, back, buttocks, and lower legs—that may be crusted, scaling, and extremely itchy.

(6) Neurodermatitis is scaly patches of skin on the head, lower legs, wrists, or forearms caused by a localized itch (such as an insect bite) that becomes intensely irritated when scratched.

(7) Stasis dermatitis is a skin irritation on the lower legs, generally related to circulatory problems.

(8) Dyshidrotic eczema is irritation of the skin on the palms of hands and soles of the feet characterized by clear, deep blisters that itch and burn.

Radiation therapy, another skin disorder, can have some unpleasant side effects in the skin. The following are the most common side effects, both acute and chronic, resulting from radiation. Unforeseen side effects may occur because of the unique and varied tolerance of individual persons. Late effects of treatment may not always be predictable and may be influenced by concurrent and/or subsequent treatment for this and other diseases.

Specific side effects of radiotherapy depend on the part of the body being treated as well as the dose given. In general, the first change is a reddening of the skin, resembling a sunburn. In many patients this is all that is experienced. However, in most patients the burn can be severe and in many cases equivalent to second degree burns. Like a sunburn, the involved area is often sensitive and even painful to the touch. In addition, the overlying skin may break down and the area may remain open until several days to weeks after the course of radiation is completed. Once the course of radiotherapy is completed, the redness will gradually go away and any open areas normally will heal. However, the skin in this area will most likely develop features of aged skin including pronounced wrinkling, skin thinning, stiffness and/or dryness, as well as possible pigmentation changes.

Most of the current treatment options for radiation dermatitis involve the use of emollients or aloe gels in an attempt to keep the skin moisturized. However, as most know who have had the experience of a sunburn, moisturization helps the skin from drying out but does not reduce the pain or redness, which are caused by inflammation. The presently disclosed and/or claimed inventive concept(s) comprises a moisturizing lotion that contains an active agent, a bioactive that is able to reduce skin redness and pain associated with radiation therapy.

Another skin disorder, hyperpigmentation, is a common and distressing condition afflicting a large subset of the population. Hyperpigmentation is the result of an increased amount of melanin in the epidermis, the dermis, or both. This pigmentary change can be divided into 2 pathophysiologic processes: melanocytosis (increased number of melanocytes) and melanosis (increased amount of melanin).

In a particular embodiment, the presently disclosed and/or claimed inventive concept(s) comprises a formulation comprising dihydroeugenol. The DHE formulation may be administered topically, systemically, or orally administered to a subject having rosacea for example for treating and reducing the rosacea on the subject's skin. The DHE formulation may also be used for example to treat and/or inhibit psoriasis and radiation dermatitis in a subject. The formulation may comprise, with or instead of the DHE, a salt, ester, or ether, thereof as described elsewhere herein. The formulation may further comprise one or more of isoeugenol (IE) or of a salt, ester, or ether thereof, for example isoeugenyl acetate or methyl isoeugenol. Any of these formulations may also be used to treat inflammatory skin conditions such as actinic keratitis, acne, scarring, allergic and irritant contact dermatitis, atopic dermatitis, erythema (sunburn), hand eczema, seborrheic dermatitis, alopecia areata, and other inflammatory irritations of the skin. Formulations comprising isoeugenol and salts, esters, and ethers thereof can be used in particular to reduce the effects of hyperpigmentation of the skin.

In particular embodiments, the compositions of the presently disclosed and/or claimed inventive concept(s) comprise synthetic and/or natural versions of the compounds dihydroeugenol (DHE) and/or isoeugenol (IE) and/or ethyl vanillin (EV), and/or salts, esters, ethers or derivatives of DHE, IE and EV, or combinations thereof and particularly salts, esters, ethers, and derivatives of DHE, IE and EV including isoeugenol acetate, for example.

In one of its compositional aspects, this presently disclosed and/or claimed inventive concept(s) is directed to pharmaceutical compositions for topical, transdermal or other systemic administration containing a pharmaceutically-acceptable carrier and DHE and/or IE and/or EV and/or salts, esters, ethers or derivatives thereof or combinations thereof as described herein. In particular, the presently disclosed and/or claimed inventive concept(s) is directed to a composition comprising DHE and/or IE and/or EV and/or salts, esters, ethers or derivatives thereof or combinations thereof for use in treating dermatologic diseases, disorders or conditions.

In one of its method aspects, this presently disclosed and/or claimed inventive concept(s) is directed to a method for treating a patient with a dermatological disease, disorder, or condition by topically administering to said patient a pharmaceutical composition comprising a pharmaceutically acceptable topical carrier and an effective dermatological disease-treating or condition-treating amount of a formulation of DHE and/or IE and/or EV and/or salts, esters, ethers, or derivatives thereof or combinations thereof.

In another one of its method aspects, this presently disclosed and/or claimed inventive concept(s) is directed to a method for treating a dermatological condition, in particular radiation dermatitis, by topically applying to a human a cosmetic composition comprising a pharmaceutically acceptable topical carrier and an effective amount of a formulation of DHE and/or IE and/or EV and/or salts, esters, ethers or derivatives thereof or combinations thereof. In still another of its method aspects, this presently disclosed and/or claimed inventive concept(s) is directed to a method for treating a patient with an inflammatory disease, disorder, or condition by systemically administering to said patient a pharmaceutical composition comprising a pharmaceutically acceptable carrier and an effective inflammatory disease-treating amount of a formulation of DHE and/or IE and/or EV and/or salts, esters, ethers, or derivatives thereof or combinations thereof.

In yet another of its method aspects, this presently disclosed and/or claimed inventive concept(s) is directed to a method for treating a human with an inflammatory disease, disorder or condition by topically applying to said human a pharmaceutical composition comprising a pharmaceutically acceptable carrier and an effective amount of a formulation of DHE and/or IE and/or EV and/or salts, esters, ethers or derivatives thereof or combinations thereof.

In yet another of its method aspects, this presently disclosed and/or claimed inventive concept(s) is directed to a method for improving the skin appearance of a person such as reducing skin aging by topically administering to said person a pharmaceutical or cosmetic composition comprising a pharmaceutically acceptable carrier and a pharmaceutically or cosmetically effective amount of a formulation of DHE and/or IE and/or EV and/or salts, esters, ethers, or derivatives thereof or combinations thereof.

In another one of its method aspects, this presently disclosed and/or claimed inventive concept(s) is directed to a method for reducing areas of hyperpigmentation on the skin by topically applying to said person's skin a pharmaceutical or cosmetic composition comprising a pharmaceutically or cosmetically acceptable carrier and an effective amount of a formulation of IE and/or salts, esters, ethers, or derivatives thereof (e.g., isoeugenol acetate) or combinations thereof.

An optional component of any of the formulations of the presently disclosed and/or claimed inventive concept(s) is cinnamaldehyde. Cinnamaldehyde may be present in any of the formulations, for example but not by way of limitation, at a concentration in the range of 0.01% to 5%. In particular, cinnamaldehyde may be included in the present formulations for use in treatment of rosacea, acne, and seborrheic dermatitis. The cinnamaldehyde provides both anti-inflammatory and anti-bacterial/anti-microbial effects against, for example, bacteria which contribute to acne and yeasts which contribute to seborrheic dermatitis.

Definitions

When describing the cosmetic and pharmaceutical compositions and methods of this presently disclosed and/or claimed inventive concept(s) as well as the compositions and methods themselves, the following terms have the following meanings:

"Ionizing radiation" refers to any radiation that ionizes the atoms or molecules of matter. It may consist of particles (such as electrons) or it may be electromagnetic (ultraviolet radiation; X-rays; gamma radiation). Ionizing radiation occurs naturally, for example as a component of sunlight, and is emitted by radioactive substances. It is also produced artificially in X-ray machines, particle accelerators, and nuclear reactors, for example.

"Isolated", when used to define the state of purity of the synthetic or natural compounds used in the practice of this presently disclosed and/or claimed inventive concept(s), means that the compounds described herein and/or salts, esters, ethers, or derivatives thereof or combinations thereof has been substantially freed of (i.e. at least about 90% and especially at least about 95%) or separated from related feedstocks, raw materials, co-products, or in the case of naturally-occurring mixtures, related materials with which the compound appears in nature.

"Pharmaceutically-acceptable topical carrier" and equivalent terms refer to an inactive liquid or cream vehicle capable of suspending or dissolving the compounds described herein and/or salts, esters, ethers, or derivatives thereof or combinations thereof and having the properties of being generally nontoxic and noninflammatory when applied to the skin. This term is specifically intended to encompass carrier materials approved for use in topical cosmetics and topical and systemic pharmaceuticals. Representative carriers include water, silicone fluids, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington's Pharmaceutical Sciences, 20th edition, 2000, Lippincott, Williams and Wilkins, which is hereby expressly incorporated herein by reference in its entirety.

"Therapeutically effective dose" means a dose of a composition of this presently disclosed and/or claimed inventive concept(s) which, when applied topically to the skin of a patient afflicted with a dermatologic or other cosmetic or medical disease, disorder, or condition, or when administered by another route such as systemically results in an observable improvement in the patient's condition.

"Topical", when used to define a mode of administration, means that a material is administered by being applied to the skin or to an internal epithelial layer such as within the rectum, or colon, or nasal or respiratory passage.

"Topically effective" means that a material, when applied to the skin or epithelial layer described above, produces a desired pharmacological result either locally at the place of application or systemically as a result of transdermal passage of an active ingredient in the material.

Where used herein, the term "oil-in-water formulation" refers to a formulation wherein a continuous water phase surrounds droplets of oil or lipid in an emulsion.

Where used herein, the term "water-in-oil formulation" refers to a formulation wherein a continuous lipid or oil phase surrounds droplets of water in an emulsion.

Where used herein the term "non-aqueous formulation" refers to a formulation having less than 1%, and particularly less than 0.1%, by weight of water in the formulation. The term "non-aqueous" is also intended to include formulations having a negligible amount of water due to absorption of atmospheric moisture.

Where used herein the term "emulsifier" refers to a compound which is used to promote and maintain a stable mixture or dispersion (emulsion) of oil droplets in a water phase, or water droplets in an oil phase.

Emulsifiers are, essentially, surfactants. These surfactants can be ionic (cationic or anionic) or non-ionic, and they can be used alone or in combination. Emulsifiers contemplated for use herein include, but are not limited to, cetearyl alcohol and sodium cetearyl sulfate, PEG-1000 monocetyl ether, glycol stearate, glyceryl stearate, cetyl alcohol, PEG-100 stearate, ceteareth-20, or quaternary ammonium salts such as alkyl trimethyl ammonium bromide, the polyol ester glycerol monostearate, potassium stearate, sodium lauryl sulfate, and ethoxylated fatty alcohols. Fatty acids like stearic acids may be included to regulate the consistency of the emulsion. Finally, polymers such as carbomers can be included in small amounts to stabilize the emulsion.

Penetration enhancers are substances which enhance passage of topically-applied compounds into the stratum, corneum of the skin and therefrom into the epidermis and dermis. Examples include, but are not limited to: dimethylisosorbide, ethoxydiglycol, 1-dodecylazacycloheptan-2-one, propylene glycol, oleyl alcohol, polyoxyethylene ester, sorbitan mono-9-octadecenoate, poly(oxy-1,2-ethanediyl) and derivatives thereof, ethanol, glyceryl monoethyl ether, monoglycerides, isopropylmyristate, lauryl alcohol, lauric acid, lauryl lactate, terpinol, menthol, D-limonene, beta-cyclodextrin, DMSO (dimethyl sulfoxide), polysorbates, fatty acids (e.g., oleic), bile salts, N-methylpyrrolidone, polyglycosylated glycerides, 1-dodecylazacycloheptan-2-one (Azone®), Cyclopentadecalactone (CPE-215®), Alkyl-2-(N,N-disubstituted amino)-alkanoate ester (NexAct®), 2-(n-nonyl)-1,3-dioxolane (DEPA®), and penetration enhancers shown for example in U.S. Pat. Nos. 3,909,816; 4,405,616; 4,801,586; 4,861,764; 4,886,783; 4,983,396; 5,118,845; and 5,196,410, each of which is hereby expressly incorporated herein by reference in its entirety.

Where the compositions and methods of the presently disclosed and/or claimed inventive concept(s) comprise isoeugenol or dihydroeugenol, the presently disclosed and/or claimed inventive concept(s) in particular contemplates methods of inhibiting or treating dermatological conditions, disorders, or diseases by epithelial application of compositions comprising esters and ethers of isoeugenol and dihydroeugenol, including, but not limited to, isoeugenyl formate, isoeugenyl acetate, isoeugenyl propionate, isoeugenyl butyrate, isoeugenyl isobutyrate, isoeugenyl oleate (and other unsaturated fatty acid esters), isoeugenyl benzoate, isoeugenyl phthalate, isoeugenyl hexanoate, isoeugenyl heptanoate, isoeugenyl octanoate, isoeugenyl pentanoate, isoeugenyl decanoate, isoeugenyl lactate, isoeugenyl cinnamate, isoeugenyl valerate, isoeugenyl isovalerate, isoeugenyl nonanoate, isoeugenyl caprylate, isoeugenyl phenylacetate, isoeugenyl anthranilate, isoeugenyl salicylate, isoeugenyl methyl ether (methyl isoeugenol), benzyl isoeugenyl ether, isoeugenyl ethyl ether (ethyl isoeugenol), and dihydroeugenyl formate, dihydroeugenyl acetate, dihydroeugenyl propionate, dihydroeugenyl butyrate, dihydroeugenyl dihydrobutyrate, dihydroeugenyl oleate (and other unsaturated fatty acid esters), dihydroeugenyl benzoate, dihydroeugenyl phthalate, dihydroeugenyl hexanoate, dihydroeugenyl heptanoate, dihydroeugenyl octanoate, dihydroeugenyl pentanoate, dihydroeugenyl decanoate, dihydroeugenyl lactate, dihydroeugenyl cinnamate, dihydroeugenyl valerate, dihydroeugenyl isovalerate, dihydroeugenyl nonanoate, dihydroeugenyl caprylate, dihydroeugenyl phenylacetate, dihydroeugenyl anthranilate, dihydroeugenyl salicylate, dihydroeugenyl methyl ether (methyl dihydroeugenol), benzyl dihydroeugenyl ether and dihydroeugenyl ethyl ether (ethyl dihydroeugenol). These esters and ethers of isoeugenol and dihydroeugenol can be combined with various carriers, vehicles, diluents, and excipients to form topical formulations as described elsewhere herein.

EXPERIMENTAL EXAMPLES

While the presently disclosed and/or claimed inventive concept(s) will now be described herein in connection with certain examples and embodiments so that aspects thereof may be more fully understood and appreciated, it is not intended that the presently disclosed and/or claimed inventive concept(s) be limited to these particular embodiments or examples. On the contrary, it is intended that all alternatives, modifications and equivalents are included within the scope of the presently disclosed and/or claimed inventive concept(s) as defined by the appended claims. Thus the examples described herein, which include particular embodiments, will serve to illustrate the practice of this presently disclosed and/or claimed inventive concept(s), it being understood that the particulars shown are by way of example and for purposes of illustrative discussion of particular embodiments of the presently disclosed and/or claimed inventive concept(s) only and are presented in the cause of providing what is believed to be the most useful and readily understood description of procedures as well as of the principles and conceptual aspects of the presently disclosed and/or claimed inventive concept(s).

Example 1

In one study, various concentrations of DHE were added to culture medium and these media were placed on human fibroblast cell cultures (results shown in FIG. 1). Cells were either not induced or induced with UVB radiation to stimulate cytokine/PGE-2 production. At 24 hours after treatment, the cell culture medium was removed and assayed by ELISA methods for the expression of PGE-2, various cytokines and chemokines.

As is shown in FIG. 1, UV radiation (UVR) treatment of fibroblasts results in a 6 fold increase in PGE-2. When DHE at a concentration as low as 10 micromolar was put into the culture media after irradiation, it completely blocked the UVR induction of PGE-2.

Figure 2:
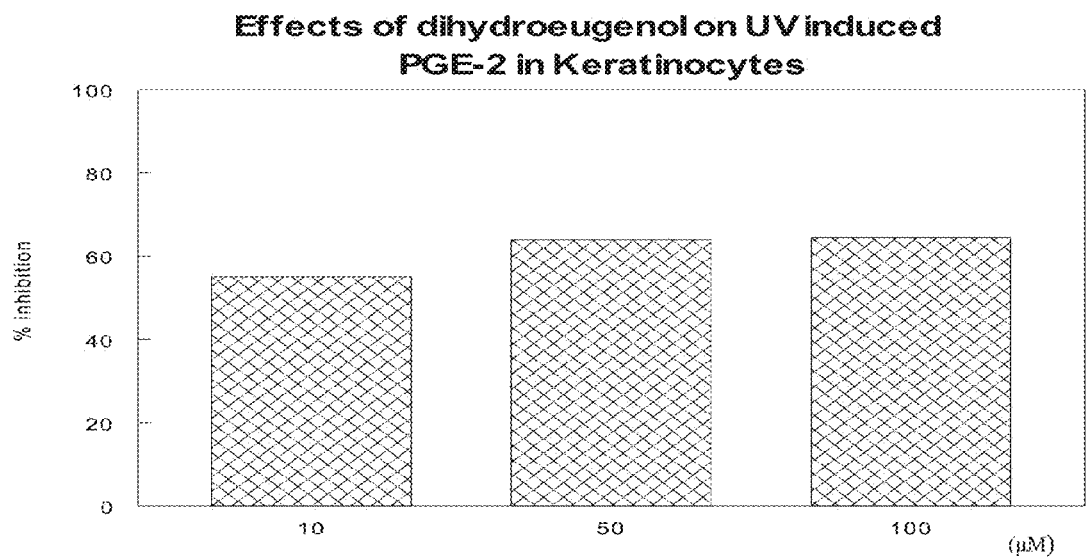
FIG. 2 is a graph showing the effects of DHE on UV-induced PGE-2 in keratinocytes.

When similar experiments were carried out with human keratinocytes, DHE was again found to markedly suppress the UVR induction of PGE-2, with a concentration of 50 uM inhibiting the production of PGE-2 by over 60% (results shown in FIG. 2). Since PGE-2 is the major inflammatory mediator responsible for sunburn these data indicate the efficacy of DHE in the treatment of sunburn. Further, since PGE-2 is known to be a principal factor in the development of actinic keratosis and skin cancer, DHE can also be used in treating these conditions.

Figure 3:
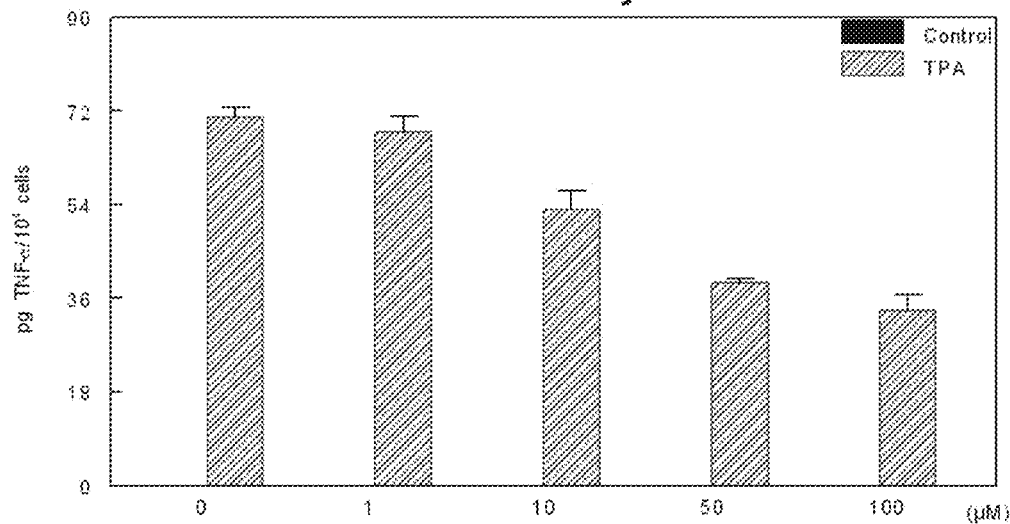
FIG. 3 is a graph showing the effects of DHE on TPA-induced TNF-α in keratinocytes.

Inflammatory mediators produced in the skin contribute to the development and propagation of such diseases as rosacea, psoriasis and atopic dermatitis. While many inflammatory mediators are involved in these diseases, TNF-α is known to be a major cytokine involved in psoriasis. For atopic dermatitis, TNF-α, IL-8, and MCP-1 are important mediators of inflammation in these diseases. DHE is effective in suppressing the TPA-induced (TPA is tetradecanolyl phorbol ester) production of TNF-α by approximately 50% at a 100 micromolar concentration (results shown in FIG. 3).

Figure 4:
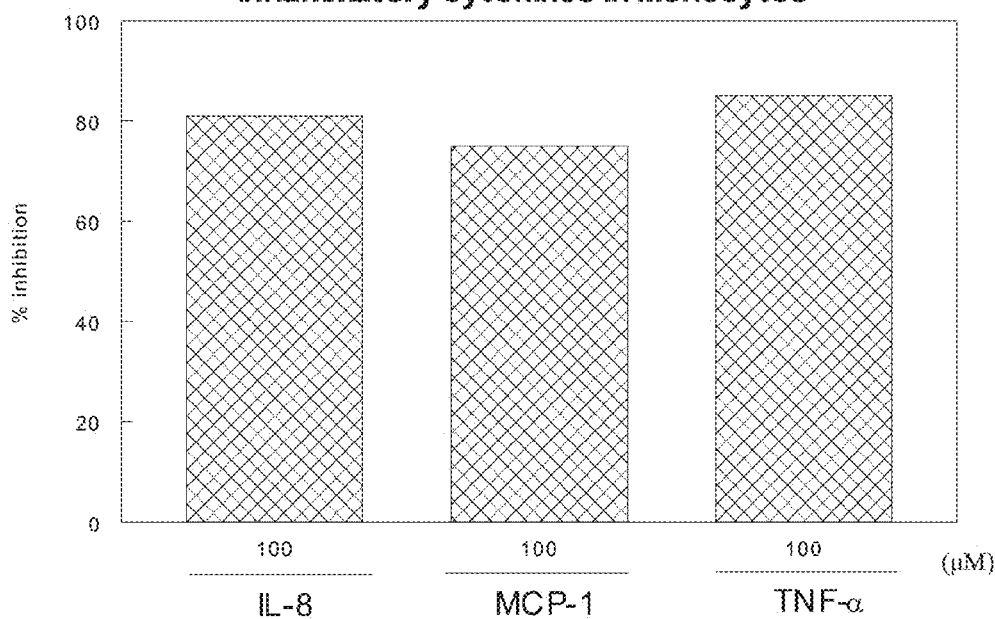
FIG. 4 is a graph showing the effects of DHE on LPS-induced inflammatory cytokines in monocytes.

In monocytes (as shown in FIG. 4), dihydroeugenol can inhibit the production of the cytokine TNF-α as well as the chemokines, IL-8, and MCP-1 (monocyte chemotactic protein 1). Since these inflammatory mediators are critically important for the development of immune driven inflammatory diseases such as atopic dermatitis and psoriasis, the results indicate that DHE can be use to treat these diseases.

A summary of some of the inflammatory mediators blocked in keratinocytes, fibroblasts and monocytes is shown below in Tables 1, 2 and 3.

Table 1 shows the inhibitory effects of DHE and IE on production of several inflammatory mediators (PGE-2, IL-6, IL-8, and TNF-α) induced in keratinocytes by exposure to TPA and UV light. DHE and IE both have inhibitory effects on production of the inflammatory mediators in keratinocytes.

TABLE 1

Percent Inhibition Of Inflammatory Mediators of Keratinocytes by DHE and IE

|  | Active Compounds | |
| --- | --- | --- |
| Concentration | DHE 100 uM | IE 100 uM |
| Keratinocytes (TPA) | | |
| PGE2 | 77% | 82% |
| IL-6 | 30% | 94% |
| IL-8 | 45% | 75% |
| TNF-α | 12% | 71% |
| Keratinocytes (UV) | | |
| PGE2 | 68% | 76% |
| IL-6 | 30% | 93% |
| IL-8 | 40% | 76% |
| TNF-α | 31% | 60% |

Table 2 shows the inhibitory effects of DHE and IE on production of several inflammatory mediators (PGE-2, IL-6, and IL-8) induced in fibroblasts by exposure to IL-1 and UV light. DHE and IE both have inhibitory effects on the production of the inflammatory mediators in fibroblasts.

TABLE 2

Percent Inhibition Of Inflammatory Mediators of Fibroblasts By DHE and IE

|  | Active Compounds | |
| --- | --- | --- |
| Concentration | DHE 100 uM | IE 100 uM |
| Fibroblasts (IL-1) | | |
| PGE-2 | 86% | 81% |
| IL-6 | 47% | 53% |
| IL-8 | 46% | 98% |
| Fibroblasts (UV) | | |
| PGE-2 | 67% | 77% |
| IL-6 | 49% | 39% |
| IL-8 | 11% | 2% |

Table 3 shows the inhibitory effects of DHE and IE on production of several inflammatory mediators (MCP-1 (monocyte chemotactic protein-1), IL-12, TNF-α, and IL-8) induced in monocytes by LPS (lipopolysaccharide) and TNF-α. DHE and IE both have inhibitory effects on the production of the inflammatory mediators in monocytes.

TABLE 3

Percent Inhibition Of Inflammatory Mediators of Monocytes By DHE and IE

|  | Active Compounds | |
| --- | --- | --- |
| Concentration | DHE 100 uM | IE 100 uM |
| Monocytes (LPS) | | |
| MCP-1 | 60% | 87% |
| IL-12 | 66% | 80% |

TABLE 3-continued

Percent Inhibition Of Inflammatory Mediators of Monocytes By DHE and IE

|  | Active Compounds | |
| --- | --- | --- |
| Concentration | DHE 100 uM | IE 100 uM |
| TNF-α | 78% | 80% |
| IL-8 | 70% | 75% |
| Monocytes (TNF-α) | | |
| MCP-1 | 46% | 82% |
| IL-8 | 72% | 78% |
| IL-12 | 98% | 100% |

Example 2

In one human clinical efficacy study the forearm of a clinical subject was irradiated at two sites with a dose of UVB radiation sufficient to induce erythema (FIG. 5). Immediately after the irradiation dose, but not before, one irradiated site was treated with a topical lotion containing 2% by weight of DHE while the other irradiated site was treated with the same topical formulation without DHE (vehicle control). After 4 hours, pronounced erythema was visible at the site treated with the vehicle control while the site treated with 2% DHE lotion displayed only minimal erythema. This result was unexpected because stronger anti-inflammatory compounds, such as steroids, when used typically are unable to prevent UVB irradiation-induced erythema even though they are more effective than DHE in blocking inflammatory mediators, including PGE-2, in vitro. Therefore, the actual mechanism of action of DHE in reducing UVB radiation induced erythema likely involves more than just inhibiting inflammatory cytokines and hormones such as PGE-2. The formulations of the presently disclosed and/or claimed inventive concept(s) not only are able to prevent induction of erythema but are also able to reverse erythema that is pre-existing.

Example 3

In addition to its ability to block radiation induced erythema (as shown in Example 2) another unexpected finding is that topically-applied DHE is effective in reducing the symptoms of rosacea, a disease whose etiology is for the most part not understood. Typical treatments for rosacea include topical metronidazole which is an antibiotic effective against bacteria and some parasites, and oral antibiotics. When topical DHE and/or a combination of DHE, IE, and cinnamaldehyde was topically applied, over 8-12 weeks, to patients suffering from rosacea, the results revealed an overall improvement in their condition with use of a DHE formulation versus the same lotion base without the DHE or DHE/IE/cinnamaldehyde. The results of this study are shown in FIG. 6A-B.

Example 4

A clinical study carried out with cancer patients undergoing radiation therapy showed that topically-applied 2% DHE lotion (applied twice daily) can almost completely prevent the onset of radiation dermatitis. For example in a patient who underwent 35 radiation treatments for breast cancer and who was treated with a 2% DHE lotion (e.g., Formulation 5 shown below) daily during the 35 radiation treatments, there was no radiation damage after the 35 days of treatment or one month after the end of radiation treatment (see FIG. 7A-C).

Example 5

The presently disclosed and/or claimed inventive concept(s) further contemplates use of various DHE, IE and EV compositions and salts, esters, ethers, and derivatives thereof to mitigate the effects of aging on the skin. For all aging studies, normal human fibroblast cell cultures were used. These cells normally produce collagen, elastin and hyaluronic acid. As the skin ages, the fibroblasts in the dermis lose their ability to produce these three key components of skin, and the skin consequently loses elasticity, thickness and smooth texture. In addition, as fibroblasts age, they increase the expression of certain enzymes that destroy collagen and elastin. There are about 13 of these enzymes, collectively referred to as MMPs (matrix metalloproteinases). One of the principal MMPs, MMP-1, is responsible for collagen degradation. For experiments herein to determine the effects of DHE, IE and EV on collagen, elastin and hyaluronic acid, fibroblasts were treated with the compounds for 72 hours, mRNA was then isolated, and analyzed for abundance by RT-PCR (Reverse transcriptase-Polymerase Chain Reaction). IE, DHE and EV were shown to stimulate collagen production in fibroblasts.

Figure 8:
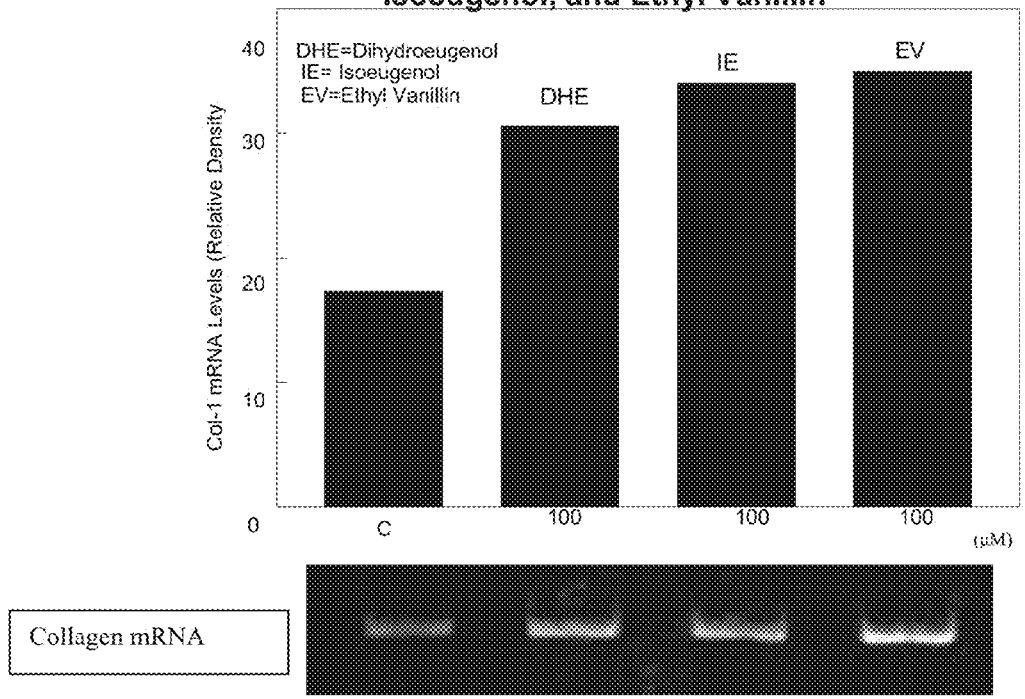
FIG. 8 is a graph showing stimulation of collagen 1 mRNA in fibroblasts by DHE, isoeugenol (IE), and Ethyl vanillin (EV).

Fibroblast cell cultures were treated with either IE, DHE or EV for 72 hours at which time the amount of collagen mRNA present in the cells was determined. DHE, IE and EV each caused stimulation of collagen production in fibroblasts, as indicated by increased collagen mRNA production (FIG. 8).

Figure 9:
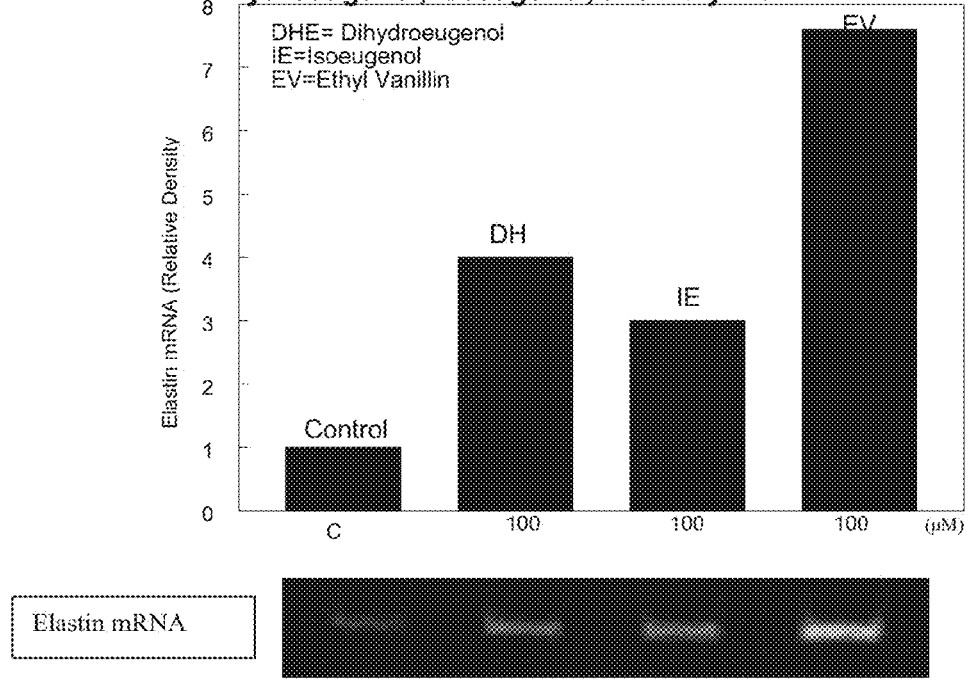
FIG. 9 is a graph showing stimulation of elastin mRNA in fibroblasts by DHE, IE and EV.

In addition to stimulating collagen mRNA synthesis and collagen protein synthesis, DHE, IE and EV and salts, esters, ethers, and derivatives thereof can increase the level of elastin mRNA in human dermal fibroblasts as shown in FIG. 9. The image is from an electrophoresis gel of DNA amplified by PCR from fibroblast mRNA. This gel was analyzed and the density of each band quantified by image analysis software. The bar graph showing the densitometric analysis is shown above the image. DHE, IE and EV increase elastin levels in human dermal fibroblasts.

Figure 10:
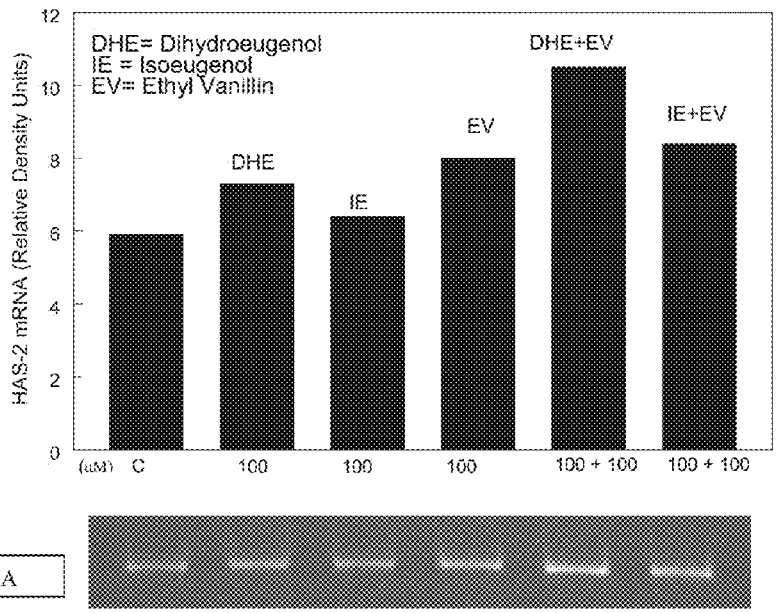
FIG. 10 is a graph showing stimulation of hyaluronic acid synthase-2 in RNA in fibroblasts by DHE, IE and EV.

DHE, IE and EV, are also shown herein to stimulate mRNA for HAS-2. HAS-2 (Hyaluronic acid synthase-2) is the enzyme that manufactures hyaluronic acid (HA) in the skin. HA is a glycosaminoglycan important for maintaining moisture and suppleness in the skin. HA has a half-life of 24 hours and thus, must be continually replaced. As the skin ages, the production of HA decreases and this causes the skin to sag and become thin. It has been discovered herein that DHE, either alone or in combination with EV, can also stimulate the HAS-2 gene, as shown in FIG. 10. In addition EV alone can stimulate HAS-2, but the combination of DHE and salts and esters thereof and EV synergistically works better than either one alone.

Figure 11:
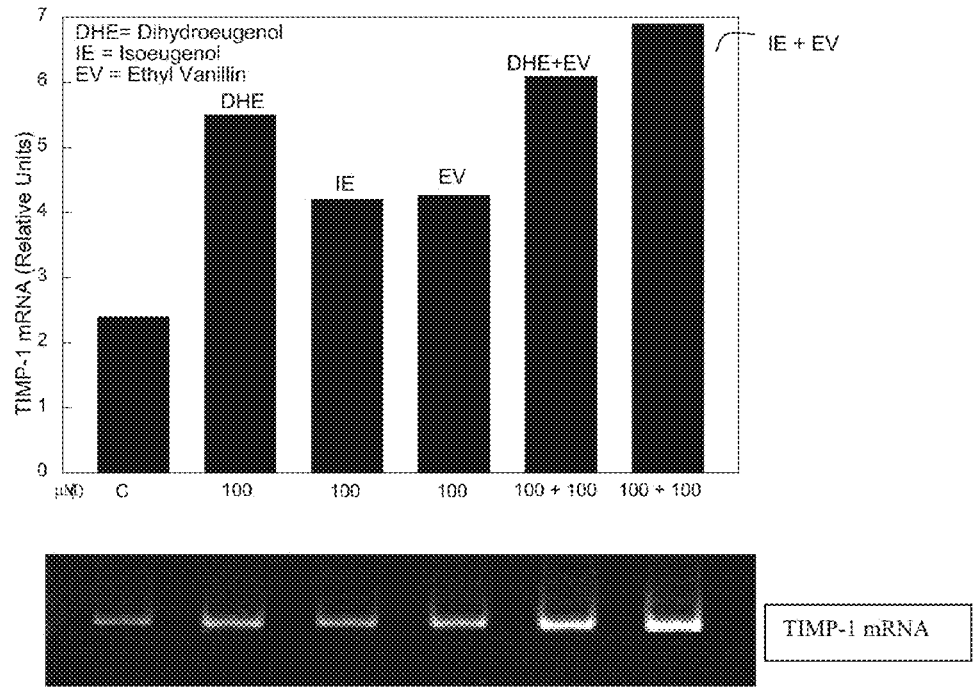
FIG. 11 is a graph showing stimulation of tissue inhibitor of metalloprotinease-1 mRNA (TIMP-1) in fibroblasts by DHE, IE and EV.

It has also been shown herein that TIMP production can be upregulated by DHE, IE and EV. Fibroblasts in the skin not only produce enzymes (MMPs) that destroy the skin matrix but they also produce proteins (Tissue Inhibitors of Metalloproteinases, i.e., TIMPS) that inhibit these enzymes. There are several TIMPs, but one that is most important for inhibiting MMPs is TIMP-1. It has been discovered that DHE, IE and EV (and salts, esters, ethers, and derivatives thereof), either alone or in combination, can significantly stimulate the production of TIMP-1, thereby providing the skin with protection against the matrix destroying activity of collagenase (MMP-1), the enzyme that TIMP-1 inhibits. Shown in FIG. 11 is PCR data showing the up-regulation of TIMP-1 mRNA by these compounds.

Figure 12:
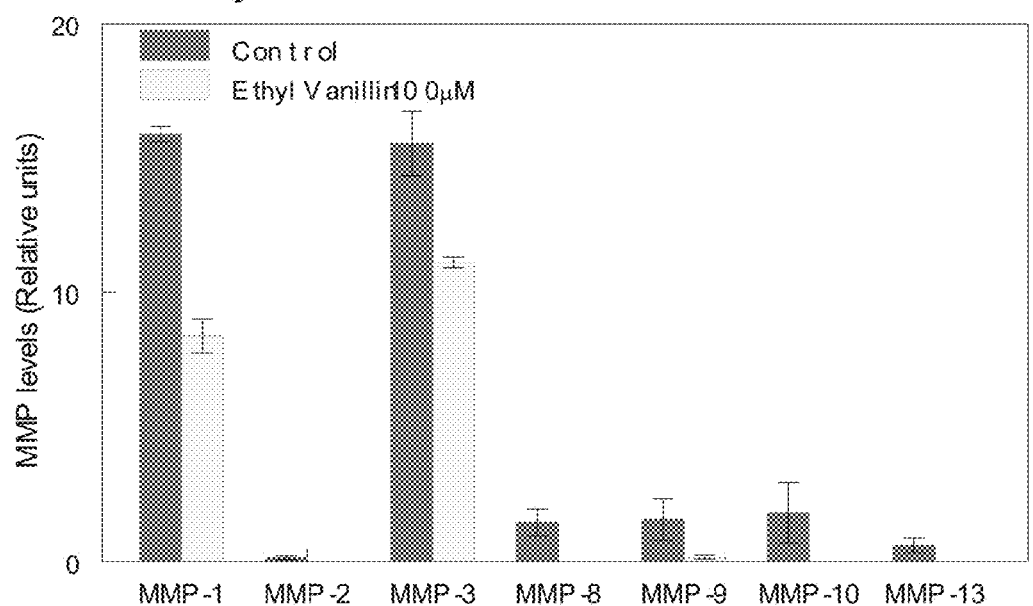
FIG. 12 is a graph showing inhibition of matrix metalloprotenases (MMPs) in fibroblasts by ethyl vanillin.

This Example also demonstrated inhibition of MMPs by EV. As mentioned above, as fibroblasts age, they increase their production of MMP enzymes that destroy collagen and elastin, particularly collagenase, MMP-1. A protein array blotting technique was utilized to determine the effect of DHE, IE and EV on the protein abundance of these enzymes. As shown below, EV is able to reduce the level of several MMPs in human dermal fibroblasts, including MMP-1, MMP-3, MMP-8, MMP-9 MMP-10 and MMP-13 (FIG. 12). This remarkable effect makes this compound an ideal addition to an anti-aging product since MMP levels in aging skin are quite high.

Example 6

IE Inhibits Melanin Synthesis

Figure 13:
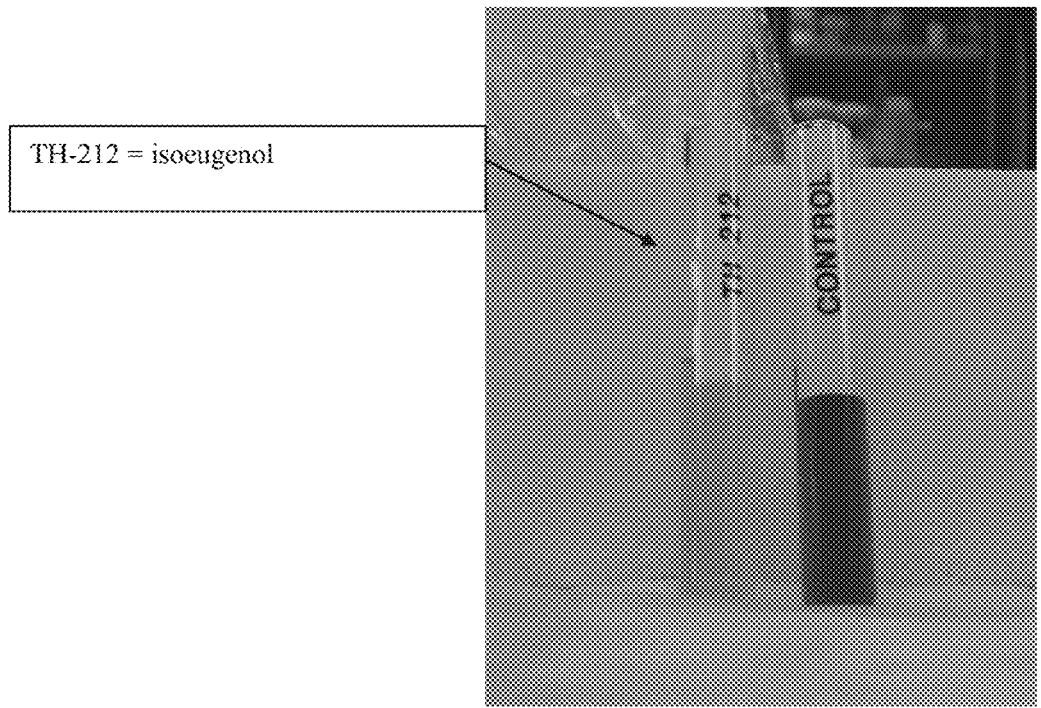
FIG. 13 is a graph showing inhibition of melanin synthesis in vitro by isoeugenol (referred to in the figure as TH-212).
Figure 14:
FIG. 14 shows photographs which demonstrate the loss of pigment in human melanocyte cultures treated with isoeugenol (TH-212) and isoeugenol acetate (referred to in the figure as TH-213) for 9 days.
Figure 16:
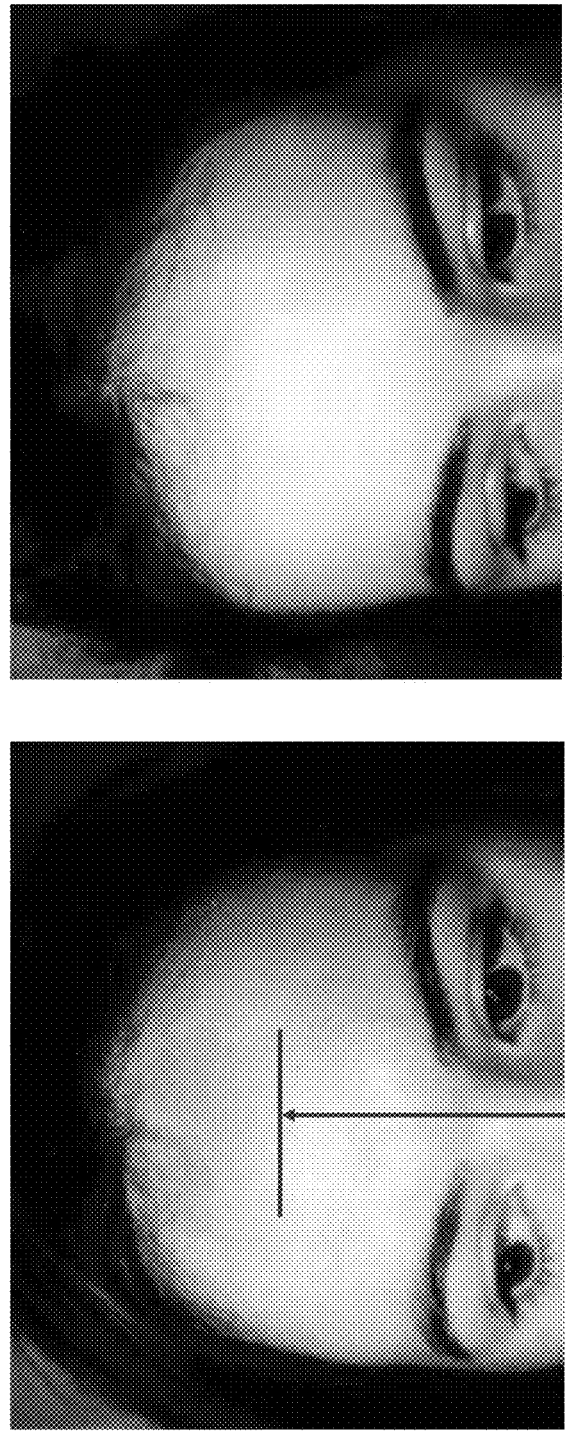
FIG. 16 shows photographs which demonstrate how a topically-applied formulation of isoeugenol acetate (TH-212 ester) plus 2% salicylic acid removes hyperpigmentation after a 30-day treatment period.
Figure 17:
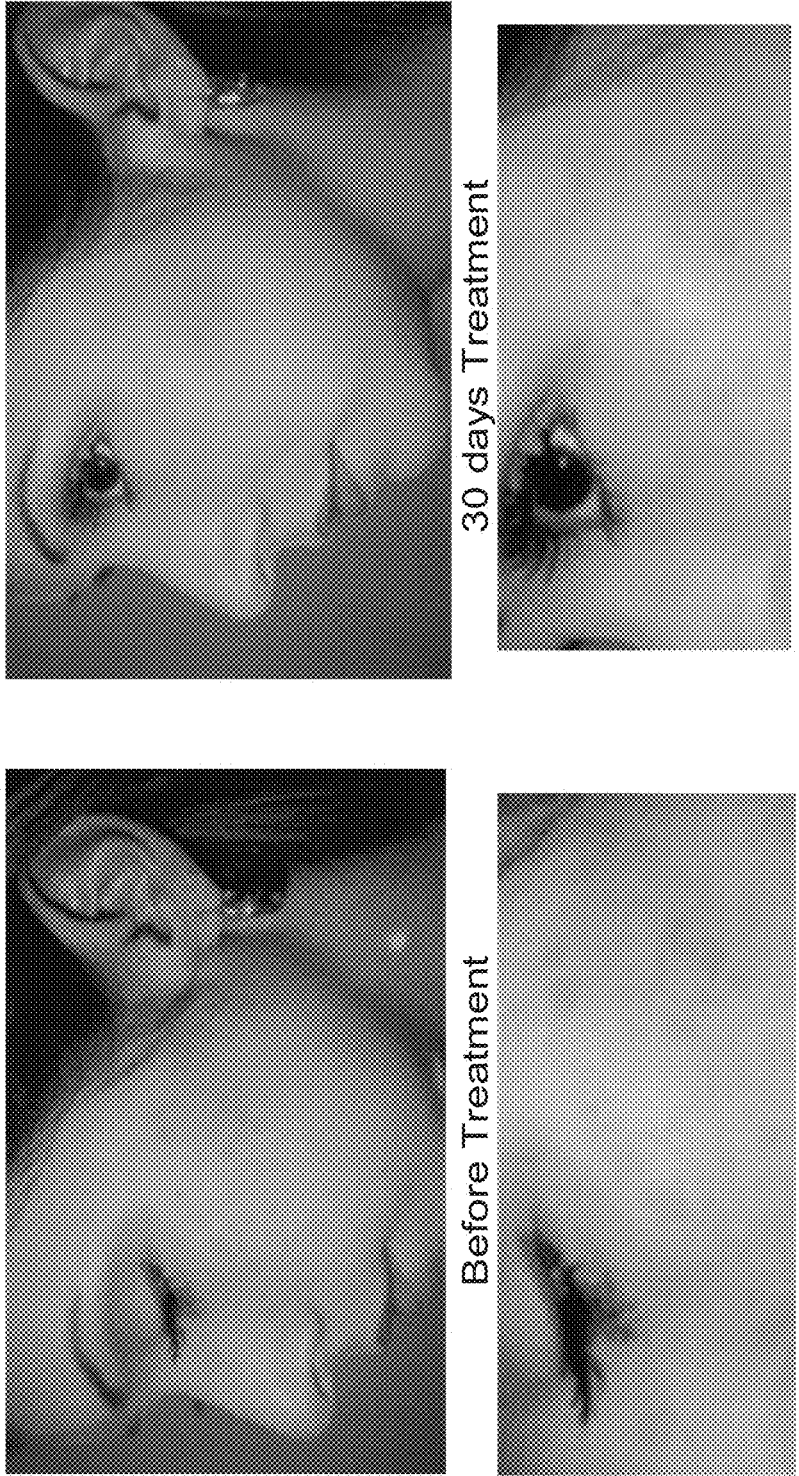
FIG. 17 shows photographs which demonstrate how a topically-applied formulation of isoeugenol acetate (TH-212 ester) plus 2% salicylic acid reduces sun-induced hyperpigmentation after a 30-day treatment period.

IE has been found to have a surprising and unexpected effect on blocking the synthesis of melanin catalyzed by tyrosinase. Two ml of a sodium phosphate buffer, pH 6.8 containing 0.2% L-DOPA (dihydroxyphenylalanine—a tyrosinase substrate) were placed in each of two test tubes. To one test tube was added 20 microliters of ethanol and to the other tube was added 20 microliters of a 1M stock of IE made up in ethanol (labeled TH-212). To start melanin synthesis from the L-DOPA substrate, 20 microliters of a tyrosinase preparation (0.5 mg/ml) was added to both tubes, the tubes were mixed and left at room temperature. The photograph in FIG. 13 was taken 2 hours after the start of the reaction. As can be seen in FIG. 13, melanin synthesis was almost completely blocked in the tube containing IE.

Without wishing to be bound by theory, it does not appear that IE is directly inhibiting tyrosinase, but rather is interfering with the post-tyrosinase steps required for melanin synthesis. IE does not appear to interfere with the tyrosinase mediated conversion of DOPA to dopaquinone or dopaquinone to dopachrome since the assay tube containing tyrosinase, DOPA and IE temporarily turns reddish. Since dopachrome is red, this indicates that IE is allowing tyrosinase to convert DOPA to dopaquinone. The conversion of dopaquinone to dopachrome is spontaneous and does not require tyrosinase. Isoeugenol may be converting dopachrome to some chemical entity that cannot proceed down the melanin synthesis pathway but remains as a colorless intermediate. Alternatively, IE may allow dopachrome to be converted to 5,6 dihydroxyindole, the next intermediate in the melanin pathway. It may then prevent the polymerization of 5,6 dihydroxyindole (a colorless intermediate) to melanin.

Figure 18:
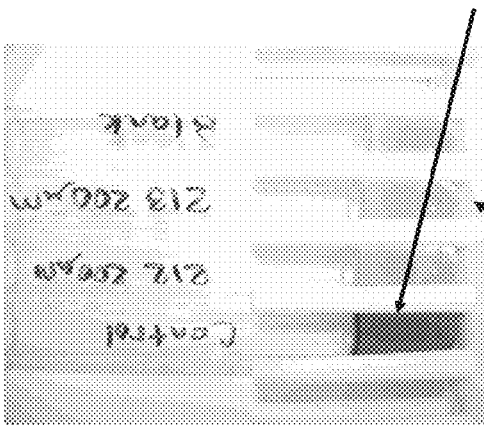
FIG. 18 shows a photograph of cell extracts treated with isoeugenol (TH-212) and isoeugenol acetate (TH-213) then provided with L-DOPA, a tyrosinase substrate. Cell lysates were prepared from human melanocytes. The amount of tyrosinase in these cell lysates was determined by DOPA oxidase assay. Results show a high level of tryosinase in Control (untreated) cell lysates, and an absence of tyrosinase activity (lack of color) in assay tubes containing cell extracts obtained from melanocytes treated with TH-212 or TH-213.

FIGS. 14-17 show the skin-lightening effects of topically-applied formulations of isoeugenol and its ester isoeugenol acetate (a.k.a. isoeugenyl acetate) in the treatment of hyperpigmented areas in the skin, wherein a reduction of melanin pigment in the skin is caused by the topical application of the formulations. In addition to blocking a post-tyrosinase step in melanin synthesis, IE and IE acetate can inhibit the expression of the tyrosinase protein in human melanocytes. This inhibitory effect can be demonstrated by preparing cell extracts from melanocytes treated for 9 days with either IE or IE-acetate or left untreated. If the cell extracts contain tyrosinase when an aliquot of extract is placed in a tube containing L-DOPA (a tyrosinase substrate) in buffer, the enzyme will convert the DOPA to melanin. The melanin will appear brownish-black in the assay tube. If IE or IE-acetate has inhibited tyrosinase synthesis in melanocytes, then the extracts from these cells will contain no enzyme and will not be able to produce melanin from DOPA in the assay tube. As shown in FIG. 18 very little melanin was made in assay tubes that contained DOPA plus cell extracts from either IE or IE-acetate treated cells. An inhibitory effect of IE or IE-acetate on tyrosinase synthesis can also be demonstrated by the use of western immunoblots. In this assay, cell extracts from human melanocytes either left untreated or treated with 200 micromolar of either IE or isoeugenol acetate for 9 days are run on SDS polyacyrlamide electrophoresis gels to separate tyrosinase from other proteins. The tyrosinase in the gel is then blotted to a membrane and the tyrosinase detected by staining with a specific anti-tyrosinase antibody. The antibody-bound tyrosinase is then visualized by chemiluminescence. The results show that while untreated melanocytes have a high abundance of tyrosinase, the melanocytes treated for 9 days with either IE or isoeugenol acetate had almost no detectable tyrosinase present. This indicates that these compounds suppress the synthesis of the enzyme in human melanocytes.

Western immunoblots of tyrosinase abundance in human melanocyte extracts treated for 9 days with isoeugenol or isoeugenol acetate showed a considerable reduction in tyrosinase (as measured by RDU-relative densitometric units). The control showed approximately 7.25 RDU, while about 200 μM concentrations of isoeugenol and isoeugenol acetate resulted in about 3 RDU and 3.75 RDU, respectively (data not shown).

Regardless of the mechanism by which IE or IE acetate or other compounds described herein have their effect, the inhibition of melanin production is essentially permanently blocked since test tubes containing DOPA, IE and tyrosinase fail to darken even after 2 weeks. The presently disclosed and/or claimed inventive concept(s) thus further contemplates topically applying an IE composition which has a skin-penetrating vehicle to reduce or prevent the formation of melanin in vivo in keratinocytes, thereby acting as a skin lightening agent.

The presently disclosed and/or claimed inventive concept(s) in particular contemplates methods of inhibiting skin pigmentation (hyperpigmentation) and causing skin lightening by topical application of compositions comprising isoeugenol and salts, esters, and ethers of isoeugenol, including, but not limited to, isoeugenyl formate, isoeugenyl acetate, isoeugenyl propionate, isoeugenyl butyrate, isoeugenyl isobutyrate, isoeugenyl oleate (and other unsaturated fatty acid esters), isoeugenyl benzoate, isoeugenyl phthalate, isoeugenyl hexanoate, isoeugenyl heptanoate, isoeugenyl octanoate, isoeugenyl pentanoate, isoeugenyl decanoate, isoeugenyl lactate, isoeugenyl cinnamate, isoeugenyl valerate, isoeugenyl isovalerate, isoeugenyl nonanoate, isoeugenyl caprylate, isoeugenyl phenylacetate, isoeugenyl anthranilate, isoeugenyl salicylate, isoeugenyl methyl ether (methyl isoeugenol), isoeugenyl ethyl ether (ethyl isoeugenol) and benzyl isoeugenyl ether. These esters and ethers of isoeugenol can be combined with various carriers, vehicles, diluents, and excipients to form topical formulations as described elsewhere herein.

Example 7

Treatment of Psoriasis

The IE and DHE compositions (and salts, esters and ethers thereof) contemplated herein can be used to treat the scaly patches which occur in the skin of sufferers of psoriasis. Clinical treatments have shown significant reduction of scaling and inflammation after a 30-day course of treatment using the compositions of Examples 4-7. For example, FIG. 19 shows before (A) and after (B) pictures of a single psoriatic skin lesion after a 30 day treatment with the formulation of the presently disclosed and/or claimed inventive concept(s) comprising DHE and IE.

Example 8

Effect of Water on Stability of EV

In a particular embodiment, the presently disclosed and/or claimed inventive concept(s) comprises a non-aqueous formulation of ethyl vanillin, particularly comprising a silicone as the primary component (e.g., for example in the range of 20%-90% silicone). The non-aqueous formulation of ethyl vanillin can be topically applied to the skin to stimulate fibroblast production of collagen, elastin, and TIMPs in the dermis and to reduce production of MMPs in the dermis, thereby inhibiting and counteracting the effects of aging of the skin and causing improved appearance thereof. In a certain embodiment, the formulation comprises 0.1 to 5% of ethyl vanillin. The formulation may further be used to "re-model" scars in the skin wherein scars in the skin (including stretch marks and scarring due to acne) are treated so as to cause them to "disappear" i.e., to regain normal skin coloration and texture. The formulation may further comprise DHE, IE, and/or salts, esters, and/or ethers thereof and cinnamaldehyde.

In a novel discovery of the presently disclosed and/or claimed inventive concept(s), it has been found that EV cannot be placed in a water-oil emulsion without the EV significantly decomposing within 24-48 hours. This surprising and unexpected finding meant that it was necessary to identify a carrier/vehicle system that would accommodate EV in a soluble form and at the same time maintain its chemical stability (defined herein as at least 95% of the ethyl vanillin remaining chemically intact for at least 3 months). In one formulation contemplated herein, EV is dissolved in caprylic/capric triglyceride or other fatty acid triglyceride and then mixed into a silicone fluid wherein the silicone is the primary (greatest percentage) component of the formulation. The cosmetic silicone fluid used in this embodiment accepts the caprylic/capric triglyceride and allows the EV to remain in solution. Because the formulation contains no water (or a negligible amount, such as less than 0.5%, due to absorption of atmospheric moisture) and no emulsifiers, the EV remains stable. Therefore, the presently disclosed and/or claimed inventive concept(s) contemplates formulations of EV in non-aqueous solutions, particularly comprising at least 20% to 25% to 30% to 35% to 40% to 45% to 50%, or up to 60%, 70%, 80% or 90% silicone thereby explicitly excluding water-in-oil, or oil-in-water, emulsions. Additionally, besides caprylic capric triglyceride, EV can be solubilized in jojoba oil, sunflower oil or squalane or any other solubilizer which is accepted by the silicones.

For example, a water-in-oil formulation in which EV decomposes within 24 hours (and thus is not a formulation of the presently disclosed and/or claimed inventive concept(s)) is:

water (62.8%), butanediol (5%), glycerin (4%), ethoxydiglycol (3%), glycereth-7 (2%), polysorbate 20 (0.2%), glyceryl stearate (and) PEG-100 stearate (4%), isocetyl stearate (3.5%), jojoba oil (3.5%), mineral oil (3%), isostearyl palmitate (3%), PEG-7 glyceryl cocoate (2%), isocetyl alcohol (2%), cetyl ricinoleate (1%), ethyl vanillin (1%).

Pharmaceutical and Cosmetic Compositions

In certain embodiments, the DHE and/or IE and/or EV compositions, and/or salts, esters, ethers, or derivatives thereof described herein are administered in the form of pharmaceutical or cosmetic compositions. Such compositions can be prepared in a manner well known to those of ordinary skill in the pharmaceutical and cosmetic arts. As noted above, the compositions may further comprise cinnamaldehyde.

Generally, the compositions of this presently disclosed and/or claimed inventive concept(s) are administered in a cosmetic amount or a therapeutically or cosmetically effective dose. The amount of the compound actually administered in a therapeutic setting may, typically be determined by a physician, such as a dermatologist in the light of the relevant circumstances, including the condition to be treated, the chosen route of administration, the actual compound administered, the age, weight, and response of the individual patient, the severity of the patient's symptoms, and the like. In cosmetic settings, the amount to be applied is selected to achieve a desired cosmetic effect.

The cosmetic compositions of this presently disclosed and/or claimed inventive concept(s) are to be administered topically (or via other epithelial administration, where desired). The pharmaceutical compositions of this presently disclosed and/or claimed inventive concept(s) are to be administered topically, transdermally or systemically such as orally or by injection or other suitable methods known by those of ordinary skill in the art.

In such compositions, the DHE and/or IE and/or EV and/or salts, esters, ethers, or derivatives thereof is usually a minor component (or components) (from about 0.001 to about 20% by weight, or particularly from about 0.01 to about 10% or 0.1% to 5%, or 1.0% to 3%, by weight), with the remainder being various vehicles or carriers and processing aids helpful for forming the desired dosing form and for carrying the active agent into the epidermis. Cinnamaldehyde may be added in amounts of 0.001% to %5, or particularly 0.01% to 1%, or more particularly 0.05% to 0.5%. One particular formulation comprises 0.4% DHE, 0.16% IE acetate, and 0.04% EV, and optimally 0.1% cinnamaldehyde.

Topical cosmetic forms and topical pharmaceutical dosing forms can include lotions, shampoos, soaks, gels, creams, ointments and pastes. Lotions commonly employ a water or alcohol base. Gels are semi-solid emulsions or suspensions. Creams generally contain a significant proportion of water in their base while ointments are commonly more oily.

Liquid forms, such as lotions suitable for topical administration or for cosmetic application, may include a suitable aqueous or non-aqueous vehicle with buffers, suspending and dispensing agents, thickeners, penetration enhancers, and the like. More solid forms such as creams or pastes or the like may include, for example, any of the following ingredients: water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

The above-described components for liquid, semisolid and solid topical compositions are merely representative. Other materials as well as processing techniques and the like are set forth in Remington's Pharmaceutical Sciences, cited above, which is hereby expressly incorporated herein by reference in its entirety.

When pharmaceutical compositions are to be administered transdermally, they typically are employed as liquid solutions or as gels. In these settings, the concentration of DHE and/or IE and or EV and/or salts, esters, ethers, or derivatives thereof ranges, individually or in combination, from about 0.1% to about 20%, such as from about 0.1% to about 10%, or from 1% to 5%, of the composition with the remainder being aqueous mixed or nonaqueous vehicle, such as alcohols and the like, suspending agents, gelling agents, surfactant, and the like. Examples of suitable such materials are described below.

The compositions comprising DHE and/or IE and/or EV or salts, esters, ethers, or derivatives thereof as defined herein can also be administered in sustained release transdermal forms or from transdermal sustained release drug delivery systems. A description of representative sustained release materials can be found in the incorporated materials in Remington's Pharmaceutical Sciences, cited above.

The compositions for systemic administration include compositions for oral administration, that is liquids and solids, and liquid compositions or suspensions for injection and formulations for rectal, colonic, vaginal, nasal, and parenteral administration.

Compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical occupant. Typical unit dosage forms include profiled, premeasured ampules or syringes of the liquid compositions or pills, tablets, capsules or the like in the case of solid compositions. In such compositions, the DHE and/or IE and/or EV and/or salts, esters, ethers, or derivatives thereof alone or in combination is usually a minor component (from about 0.01 to about 20% by weight or from about 0.1 to about 10% by weight or 1% to 5% by weight), with the remainder being various vehicles or carriers and processing aids helpful for forming the desired dosing form.

Liquid forms suitable for oral administration may include, but are not limited to, a suitable aqueous or non-aqueous vehicle with buffers, suspending and dispensing agents, colorants, flavors and the like. Solid forms may include, but are not limited to, any of the following ingredients, or compounds of a similar nature: a binder such as microcrystalline cellulose, gum tragacanth or gelatin; an occupant such as starch or lactose; a disintegrating agent such as alginic acid, Primogel™, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the DHE and/or IE and/or EV and/or salts, esters, ethers, or derivatives thereof in such compositions are typically minor components, often being from about 0.005 to 10% by weight, or 0.1 to 2% by weight, for example, with the remainder being the injectable carrier and the like.

The above-described compositions for orally or epidermally administrable or injectable compositions are merely representative. Other materials as well as processing techniques and the like are set forth in the part of Remington's Pharmaceutical Sciences, cited above.

The following formulation examples illustrate representative cosmetic and pharmaceutical compositions of this presently disclosed and/or claimed inventive concept(s). The presently disclosed and/or claimed inventive concept(s), however, is not limited to the following pharmaceutical compositions.

EXEMPLARY FORMULATIONS

Formulation 1—Lotion

In a particular embodiment, DHE was formulated into a topical lotion a 2% final concentration and tested for its ability to block a UVB-irradiation induced sunburn. Volunteers were irradiated with a UVB radiation source sufficient to produce a sunburn (approximately a 3 MED dose) and after irradiation 1 ml of a 2% topical DHE lotion was applied to one of two sites. Another irradiated site was left untreated. By 2-6 hours erythema was noted in the untreated UVB site while the side treated with the topical DHE lotion showed no erythema.

Formulation 2—Liquid

A formulation of DHE (125 mg total), and xanthan gum (4 mg) are blended, passed through a No. 10 mesh U.S. sieve, and then mixed with a previously made solution of microcrystalline cellulose and sodium carboxymethyl cellulose (11:89, 50 mg) in a water/isopropanol (75:25) mixture. Sufficient water/isopropanol and salicylic acid to 2% by weight or a sufficient amount to maintain a pH of 3-6.5 are then added to produce a total volume of 5 mL.

Formulation 3—Cream

A commercial mineral oil-water cold cream base is obtained. To 100 grams of this base, 1 gm of DHE and/or IE and/or EV and/or salts, esters or derivatives thereof as a fine powder or liquid, is added with continuous mixing and stirring to suspend the powder in the base yielding a cosmetic or pharmaceutical composition.

In one embodiment, this composition includes the following: deionized water (55.6% by weight); niacinamide (2.0%); glycerin (4.0%); phenonip (1.0%); propylene glycol (5.0%); transcutol (3.2%); jojoba Oil (3.5%); isocetyl alcohol (2.0%); isocetyl stearate (3.5%); mineral oil (3.0%); dihydroeugenol (1.0%); salicylic acid (2%); isostearyl palmitate (3.0%); PEG-7 glyceryl cocoate (2.0%); Glycereth-7 (2.0%); POLYSORBATE-20® (0.2%); cetyl ricinoleate (1.0%); glyceryl stearate/PEG-100 stearate (4.0%); and SEPIGEL® (2.0%).

Formulation 4—Cream

Deionized water (56.4% by weight); caffeine (1.0%); butanediol (4.0%); glycerin (1.0%); phenonip (1.0%); POLYSORBATE-20® (0.2%); niacinamide (2.0%); arlacel (6.0%); isocetyl stearate (3.5%); cetyl ricinoleate (1.0%); protaderm B (10.0%); jojoba oil (3.5%); stearyl alcohol (3.0%); cetearyth 20 (0.4%); PEG-12 (3.0%); dihydroeugenol (2.0%); SEPIGEL™ (2.0%).

Formulation 5—Cream

Water (44.4% by weight); niacinamide (2.0%); propylene glycol (3%); PEG-100 stearate (1%); ajidew (1%); glycerin (1%); EDTA (0.1%); carbopol (20%); squalene (2%); jojoba oil (2%); stearic acid (2%); glyceryl stearate (1%); cetyl alcohol (1.5%); vitamin E (1%); dimethicone (1%); caprylic/capric triglyceride (2%); dihydroeugenol (2%); petrolatum (1%); promulgen D (2%); PP2 (2%); glycol stearate (1%); dimethyl isosorbide-DMI (3%); and added after emulsion: germaben (1%)<55°; and triethanolamine (1%).

Formulation 6—Tablets

A formulation of DHE and/or IE and/or EV and/or salts, esters or derivatives thereof and salicylic acid to maintain a pH of 3-6.5 is mixed with dry gelatin binder and starch diluent in a 0.1:1:1 weight ratio. A lubricating amount of magnesium stearate is added and the mixture is tableted into 210 mg tablets containing 10 mg of DHE, IE or EV or other compounds described herein.

Formulation 7—Injection

A formulation of DHE and/or IE and/or salts, esters or derivatives thereof, and salicylic acid to maintain a pH of 3-6.5, is dissolved in injectable aqueous saline medium at a concentration of 1 mg/ml.

Ethyl Vanillin (EV) Formulations—Topical

The following are five non-aqueous formulations comprising EV which maintain EV in a chemically-stable condition.
1. Cyclomethicone (and) dimethiconol (20-90%), caprylic/capric triglyceride (1-20%), dimethicone (1-10%), ethyl vanillin (0.1-5%).
2. Cyclomethicone (and) dimethiconal (5-60%), cylcopentasiloxane (and) dimethicone crosspolymer (5-60%), caprylic/capric triglyceride (1-20%), dimethicone (1-10%), jojoba oil (1-10%), squalane (1-10%), ethyl vanillin (0.1-5%).
3. SD alcohol (5-50%), cetearyl octanoate (1-10%), vitamin E (0.5%), cyclomethicone (10-50%), PPG-26 oleate (1-10%), caprylic/capric triglyceride (1-10%), ethyl vanillin (0.1-5%).
4. PPG-15 Stearylether cyclomethicone (10-50%), Sunflower oil (10-50%), isopropyl alcohol (1-10%), isostearyl palmitate (1-10%), ethyl vanillin (0.1-5%).
5. Benzyl laurate (5-25%), PPG-10 butanediol (1-10%), mineral oil (10-70%), squalane (1-10%), caprylic/capric triglyceride (1-10%), ethyl vanillin (0.1-5%).

Utility and Dosing

The composition and methods of this presently disclosed and/or claimed inventive concept(s) can be used topically to treat dermatological conditions such as actinic keratitis, acne, scarring, allergic contact dermatitis, atopic dermatitis, contact dermatitis, erythema (sunburn), hand eczema, itch, irritant contact dermatitis, psoriasis, seborrheic eczema (dermatitis), other eczemas, rosacea, hyperpigmentation, alopecia areata, damage from radiation (radiation dermatitis) including UV radiation, IR radiation and any other ionizing radiation and the like, and other dermatological conditions described elsewhere herein.

The compositions, both cosmetic and pharmaceutical, can also be used to treat and inhibit sunburn and to treat and prevent other forms of UV-induced inflammation and damage as well as damage from other forms of ionizing radiation.

In these applications the cosmetic and pharmaceutical compositions are administered topically to achieve a desired cosmetic effect or a topical therapeutic effect.

In these uses the dose levels or application levels can be expressed in terms of the amount of DHE and/or IE and/or EV and/or salts, esters, ethers, or derivatives thereof delivered to the skin. For example, 1 to about 5 doses or applications per day, each containing from about 0.001 g to about 1 gram of each of DHE and/or IE and/or EV or salts, esters, ethers, or derivatives thereof or combinations thereof can be used.

Alternatively, dose levels can be expressed in terms of the volume of formulated composition administered. For example, 1 to about 5 doses or applications per day, each containing from about 1 to about 30 grams of composition containing alone or in combination from about 0.01% to about 10% by weight of each of DHE and/or IE and/or EV and/or salts, esters, ethers, or derivatives thereof and especially from 0.02% to about 8% by weight or 0.1% to 5% by weight, or 1.0 to 4% by weight.

When used in sun care products, such as suncare lotion, the concentration of DHE and/or IE and/or EV or salts, esters, ethers, or derivatives thereof can be as set forth above and the product can be applied as needed based on the intensity and duration of sun exposure before, during, or after sun exposure.

Additionally, since the DHE and/or IE and/or EV or salts, esters, ethers, or derivatives thereof have been discovered to effectively inhibit the release of cytokines, such a IL-la or others cited herein, such compounds are useful for treating diseases characterized by an overproduction or a dysregulated production of cytokines, particularly IL-la wherein treatment causes reduction of said cytokines. Elevated levels of IL-la and other cytokines, as noted above, are associated with a wide variety of inflammatory conditions, including rheumatoid arthritis, septic shock, erythema nodosum leprosy, septicemia, adult respiratory distress syndrome (ARDS), inflammatory bowel disease (IBD), uveitis, damage from ionizing radiation and the like.

In the case of transdermal administration to treat such inflammatory conditions, one can administer a quantity of composition of the presently disclosed and/or claimed inventive concept(s) to a surface area of skin suitable to achieve an effective systemic bloodstream concentration of DHE and/or IE and/or EV, or salts, esters, ethers, or derivatives thereof, e.g., of from about 0.5 µM to about 1000 µM or from about 1 µM to about 500 µM, or other concentrations noted herein. In formulations to be applied topically or systemically, it may be preferred (in certain, non-limiting embodiments) that the skin layer (epidermis and/or dermis) to be affected by the active agent maintain a concentration of active agent therein in a range of from 1 µM to 1000 µM, such as from 10 µM to 500 µM, or from 50 µM to 300 µM, or between 100 µM to 200 µM.

Injection dose levels for treating inflammatory conditions can range from (but are not limited to) about 0.01 mg/kg/hour to at least 1 mg/kg/hour, all for from about 1 to about 120 hours and especially 24 to 96 hours. A preloading bolus of from, for example, about 0.01 mg/kg to about 1 mg/kg or more may also be administered to achieve adequate steady state levels.

With oral dosing, one to five, two to four, or typically three oral doses per day are representative regimens. Using these dosing patterns, each dose may provide from about 0.01 to about 10 mg/kg of the DHE and/or IE and/or EV or salts, esters, ethers, or derivatives thereof, with particular doses each providing from about 0.01 to about 5 mg/kg, or other dosages described herein.

The DHE and/or IE and/or EV or salts, esters, ethers, or derivatives thereof can be administered as the sole active agent or they can be administered alone or in combination, or in combination with other active agents.

Although the presently disclosed and/or claimed inventive concept(s) and its advantages have been described in detail with reference to certain exemplary embodiments and implementations thereof, it should be understood that various changes, substitutions, alterations, modifications, and enhancements can be made to the presently disclosed and/or claimed inventive concept(s) described herein without departing from the spirit and scope of the presently disclosed and/or claimed inventive concept(s) as defined by the appended claims. Moreover, the scope of the presently disclosed and/or claimed inventive concept(s) is not intended to be limited to the particular embodiments of the process, compositions of matter, means, methods and steps described in the specification. As one of ordinary skill in the art will readily appreciate from the disclosure of the presently disclosed and/or claimed inventive concept(s) many equivalent processes, compositions of matter, means, methods, or steps, presently existing or later to be developed that perform substantially the same function or achieve substantially the same result as the corresponding embodiments described herein may be utilized according to the presently disclosed and/or claimed inventive concept(s) disclosed herein. Accordingly, the appended claims are intended to include within their scope all such equivalent processes, compositions of matter, means, methods, or steps.

What is claimed is:

1. A method of treating hyperpigmentation in a subject's skin, the method comprising:
    topically administering an effective hyperpigmentation-treating amount of a transdermal composition to a portion of the subject's skin which is affected by the hyperpigmentation, wherein the transdermal composition comprises:
        an active agent comprising at least one of an isoeugenol ester and a salt thereof; and
        a pharmaceutically-acceptable carrier or vehicle in which the active agent is suspended or dissolved.

2. The method of claim 1, wherein the active agent further comprises at least one of:
    (a) isoeugenol and/or a salt thereof; and
    (b) soluble ethyl vanillin and/or a salt thereof and/or an ester thereof.

3. The method of claim 1, wherein the transdermal composition comprises at least one of a penetration enhancer, cinnamaldehyde, and salicylic acid.

4. The method of claim 1, wherein the pharmaceutically-acceptable carrier or vehicle of the transdermal composition comprises a silicone.

5. The method of claim 1, wherein the active agent is maintained in the epidermis or dermis of the skin at a concentration in a range of from 1 µM to 1000 µM.

6. A method of treating hyperpigmentation in a subject's skin, the method comprising:
    topically administering an effective hyperpigmentation-treating amount of a transdermal composition to a portion of the subject's skin which is affected by the hyperpigmentation, wherein the transdermal composition comprises:
an active agent comprising at least one of isoeugenol and a salt thereof; and
a pharmaceutically-acceptable carrier or vehicle in which the active agent is suspended or dissolved.

7. The method of claim 6, wherein the active agent comprises isoeugenol.

8. The method of claim 6, wherein the active agent further comprises soluble ethyl vanillin and/or a salt thereof and/or an ester thereof.

9. The method of claim 6, wherein the transdermal composition comprises at least one of a penetration enhancer and cinnamaldehyde.

10. The method of claim 6, wherein the transdermal composition further comprises salicylic acid.

11. The method of claim 6, wherein the pharmaceutically-acceptable carrier or vehicle of the transdermal composition comprises a silicone.

12. The method of claim 6, wherein the active agent is maintained in the epidermis or dermis of the skin at a concentration in a range of from 1 μM to 1000 μM.

* * * * *

UNITED STATES PATENT AND TRADEMARK OFFICE
CERTIFICATE OF CORRECTION

PATENT NO. : 9,980,887 B2  
APPLICATION NO. : 15/236967  
DATED : May 29, 2018  
INVENTOR(S) : Bryan B. Fuller Page 1 of 1

It is certified that error appears in the above-identified patent and that said Letters Patent is hereby corrected as shown below:

In the Specification

Column 23, Line 35: Delete "IL-1a" and replace with -- IL-1α --

Column 23, Line 38: Delete "IL-1a" and replace with -- IL-1α --

Column 23, Line 40: Delete "IL-1a" and replace with -- IL-1α --

Signed and Sealed this  
Twenty-fourth Day of July, 2018

Andrei Iancu  
*Director of the United States Patent and Trademark Office*